US010182847B2

(12) United States Patent
Aferzon

(10) Patent No.: US 10,182,847 B2
(45) Date of Patent: Jan. 22, 2019

(54) POLYAXIAL VERTEBRAL ANCHOR ASSEMBLY WITH VERTICAL ADJUSTMENT AND SPLIT LOCK

(75) Inventor: Joseph Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 0 days.

(21) Appl. No.: 13/222,726

(22) Filed: Aug. 31, 2011

(65) Prior Publication Data
US 2012/0059421 A1 Mar. 8, 2012

Related U.S. Application Data

(60) Provisional application No. 61/402,717, filed on Sep. 3, 2010.

(51) Int. Cl.
A61B 17/70 (2006.01)
(52) U.S. Cl.
CPC ...... A61B 17/7035 (2013.01); A61B 17/7041 (2013.01)
(58) Field of Classification Search
CPC .................................. A61B 17/70–17/7046
USPC ........................................ 606/246, 264–279
See application file for complete search history.

(56) References Cited

U.S. PATENT DOCUMENTS

| 5,545,167 | A | 8/1996 | Lin |
| 5,549,608 | A | 8/1996 | Errico et al. |
| 5,609,593 | A | 3/1997 | Errico et al. |
| 5,609,594 | A | 3/1997 | Errico et al. |
| 5,882,350 | A | 3/1999 | Ralph et al. |
| 5,885,286 | A | 3/1999 | Sherman et al. |
| 6,063,090 | A | 5/2000 | Schlapfer |
| 6,187,005 | B1 | 2/2001 | Brace et al. |
| 6,214,012 | B1 | 4/2001 | Karpman et al. |
| 6,368,321 | B1 | 4/2002 | Jackson |

(Continued)

FOREIGN PATENT DOCUMENTS

WO WO 2007/022790 A1 3/2007

OTHER PUBLICATIONS

International Search Report and Written Opinion issued in PCT/US2011/050025 dated Dec. 22, 2011.

(Continued)

Primary Examiner — Jan Christopher Merene
Assistant Examiner — Steven Cotroneo
(74) Attorney, Agent, or Firm — Hoffman & Baron, LLP

(57) ABSTRACT

A polyaxial vertebral assembly that includes a polyaxial vertebral anchor and an articulating connector. The anchor is configured to penetrate and secure to a vertebra, and includes a spherical head end. The connector includes a base, an extension, and a common trajectory split lock. The split lock includes a first lock and a second lock. The first lock is configured to engage rigidly the base in a selected pivotal configuration to the head end along the second axis of the extension, wherein the head end is disposed in the base in the selected pivotal configuration with respect to the first axis of the base. The second lock is configured to engage rigidly a stabilizing rod at selected configurable height and rotational configuration with respect to the polyaxial vertebral anchor along the second axis, wherein the pivotal configuration and the height and rotational configuration are independently adjustable along the second axis.

21 Claims, 8 Drawing Sheets

(56) References Cited

U.S. PATENT DOCUMENTS

| | | | |
|---|---|---|---|
| 6,478,798 B1 | 11/2002 | Howland | |
| 6,976,817 B1 | 12/2005 | Grainger | |
| RE39,089 E | 5/2006 | Ralph et al. | |
| 7,121,755 B2 | 10/2006 | Schlapfer et al. | |
| 7,163,538 B2 * | 1/2007 | Altarac | A61B 17/7035 606/86 A |
| 7,186,255 B2 * | 3/2007 | Baynham | A61B 17/7035 606/266 |
| 7,306,603 B2 | 12/2007 | Boehm, Jr. et al. | |
| 7,306,606 B2 | 12/2007 | Sasing | |
| 2002/0143341 A1 * | 10/2002 | Biedermann et al. | 606/73 |
| 2003/0045879 A1 * | 3/2003 | Minfelde | A61B 17/7041 606/278 |
| 2003/0216735 A1 | 11/2003 | Altarac et al. | |
| 2004/0097933 A1 | 5/2004 | Lourdel et al. | |
| 2004/0138662 A1 | 7/2004 | Landry et al. | |
| 2004/0162560 A1 | 8/2004 | Raynor et al. | |
| 2004/0193160 A1 | 9/2004 | Richelsoph | |
| 2004/0210216 A1 * | 10/2004 | Farris | A61B 17/7038 606/264 |
| 2004/0225289 A1 | 11/2004 | Biedermann et al. | |
| 2004/0236330 A1 | 11/2004 | Purcell et al. | |
| 2005/0065517 A1 | 3/2005 | Chin | |
| 2005/0154389 A1 | 7/2005 | Selover et al. | |
| 2005/0216003 A1 | 9/2005 | Biedermann et al. | |
| 2005/0234451 A1 | 10/2005 | Markworth | |
| 2006/0036244 A1 | 2/2006 | Spitler et al. | |
| 2006/0095038 A1 | 5/2006 | Jackson | |
| 2006/0149237 A1 | 7/2006 | Markworth et al. | |
| 2006/0149241 A1 | 7/2006 | Richelsoph et al. | |
| 2006/0167455 A1 * | 7/2006 | Clement | A61B 17/7037 606/264 |
| 2007/0093826 A1 | 4/2007 | Hawkes et al. | |
| 2007/0244482 A1 | 10/2007 | Aferzon | |
| 2007/0270813 A1 | 11/2007 | Garamszegi | |
| 2008/0004625 A1 | 1/2008 | Runco et al. | |
| 2008/0009862 A1 | 1/2008 | Hoffman | |
| 2009/0062860 A1 | 3/2009 | Frasier et al. | |
| 2010/0030275 A1 * | 2/2010 | Winslow et al. | 606/264 |
| 2010/0036426 A1 | 2/2010 | Mitchell et al. | |

OTHER PUBLICATIONS

European Search Report issued in European Application No. 18166253.7-1132 dated Nov. 7, 2018.

* cited by examiner

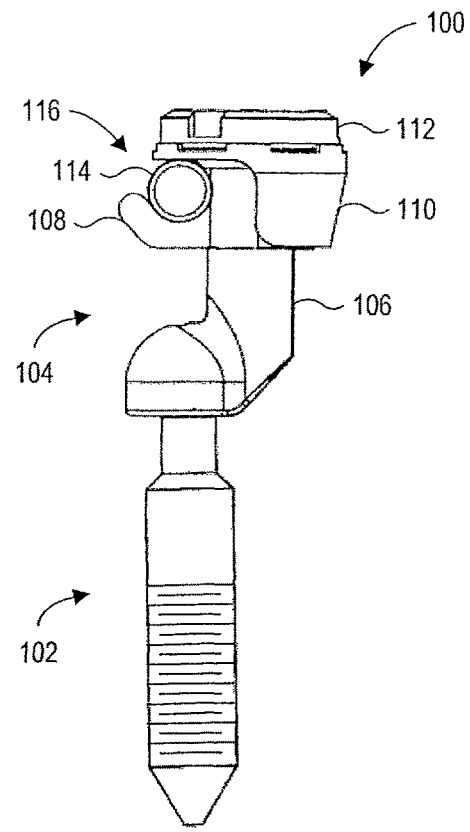
FIG. 1
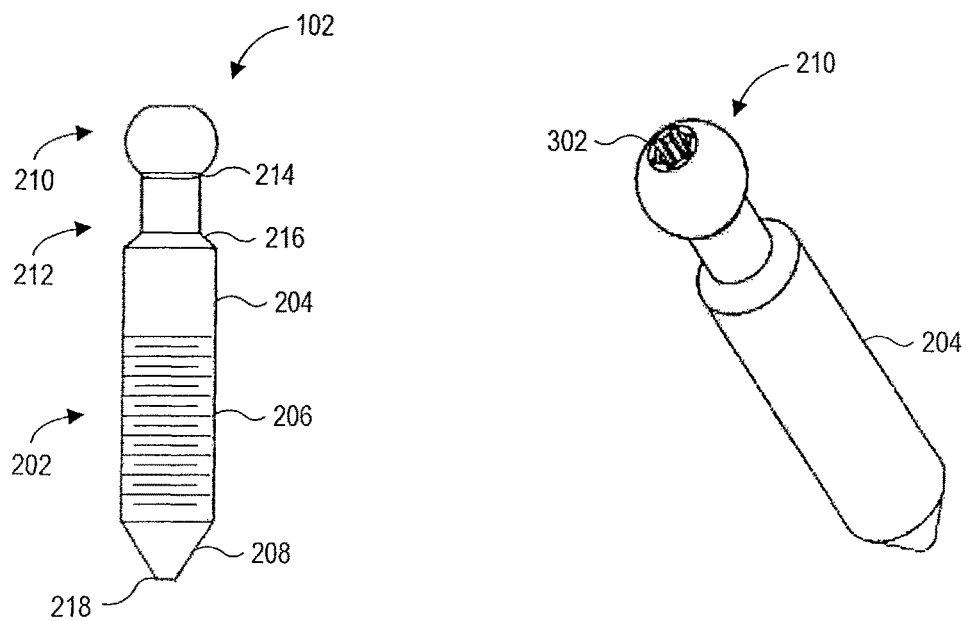
FIG. 2
FIG. 3

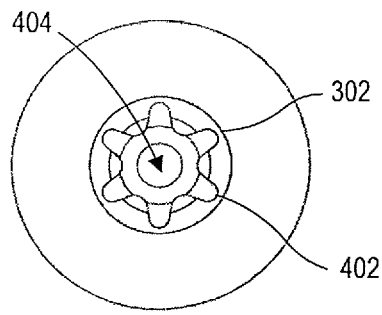
FIG. 4
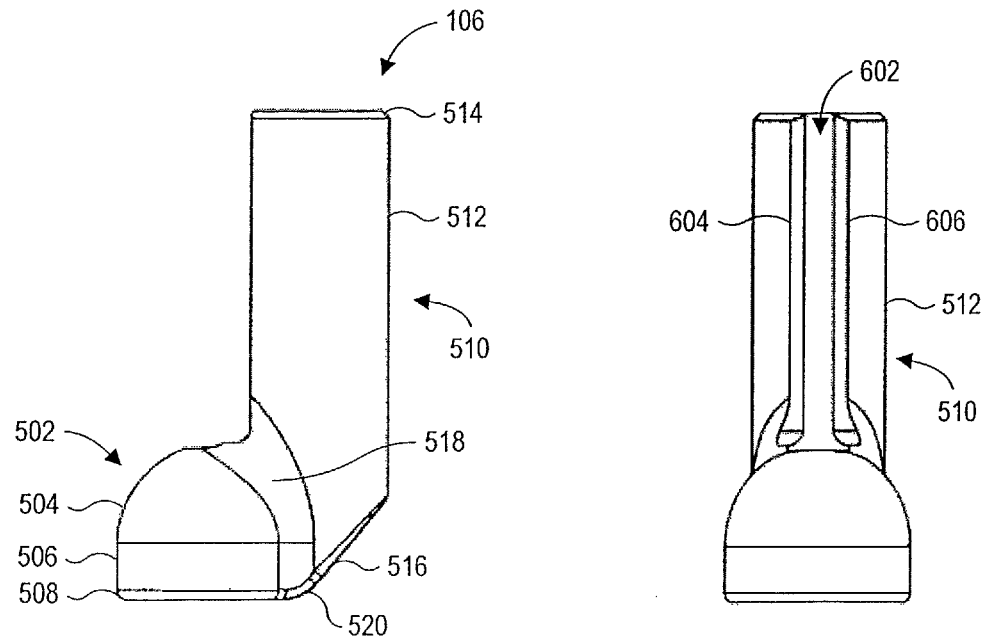
FIG. 5
FIG. 6

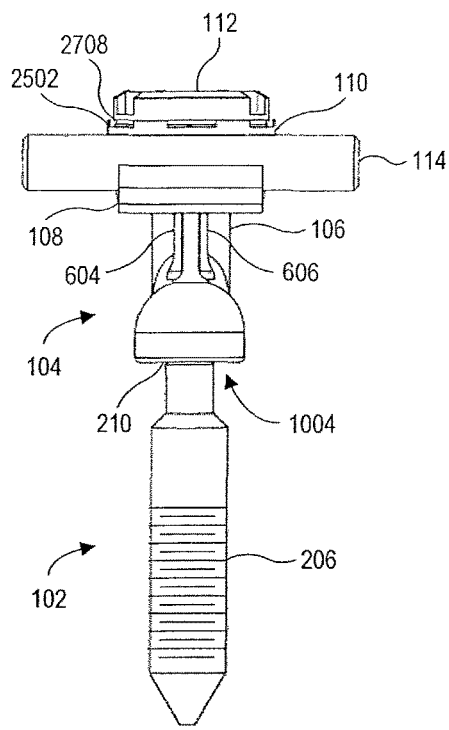
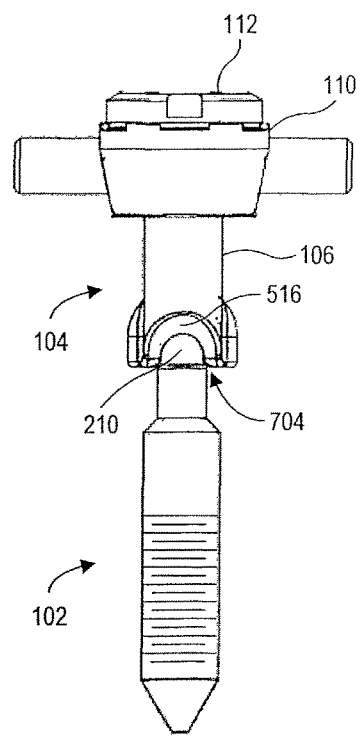
FIG. 29　　　　　　　　FIG. 30
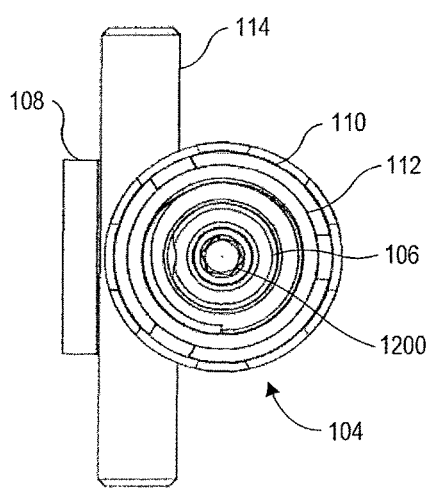
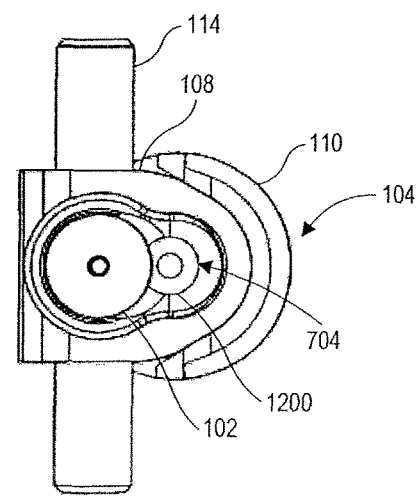
FIG. 31　　　　　　　　FIG. 32

POLYAXIAL VERTEBRAL ANCHOR ASSEMBLY WITH VERTICAL ADJUSTMENT AND SPLIT LOCK

CROSS REFERENCE TO RELATED APPLICATION

This application claims the benefit of and priority to U.S. Provisional Application No. 61/402,717 filed on Sep. 3, 2010, which is incorporated herein by reference in its entirety.

BACKGROUND

Field

The present application relates to spinal fixation devices. More specifically, the present application is directed to a polyaxial vertebral anchor assembly with vertical adjustment and split lock.

Brief Discussion of Related Art

Spinal fusion and/or deformity corrective surgery often requires securing various implants to the vertebrae. One of such implants is a pedicle screw and its related components. Pedicle screws are secured to the vertebrae involved in the surgery. The components, such as one or more stabilizing rods, are then secured to the pedicle screws via respective rod-holder assemblies in order to reduce or eliminate movement between and among neighboring vertebrae necessary for spinal fusion and/or deformity correction.

Because of the complex curvature and anatomy of the spine (e.g., lordosis), it is difficult to align certain pedicle screws and their associated rod-holder assemblies with the stabilizing rod, particularly when spanning multiple vertebrae. More specifically, the anatomy of the spine in individual patients makes it difficult and often impossible to align the pedicle screws in a single plane. The pedicle screws generally project with variable medial-lateral displacements and different angulations.

Traditionally, this type of alignment required extensive bending and test fitting (e.g., contouring) of the stabilizing rods to correctly approximate and connect to the rod-holder assemblies of the respective monoaxial pedicle screws.

More recently, polyaxial pedicle screws have enabled the rod-holder assembly to pivot about the pedicle screw's head. Such pivoting allows the rod-holder assembly to interface the stabilizing rod with minimal contouring of the stabilizing rod. Polyaxial pedicle screws have become widely available and are now the most common type of pedicle screws used in spinal fusion and/or deformity corrective surgeries.

While a polyaxial pedicle screw enables its associated rod-holder assembly to pivot about the pedicle screw's head, the rod-holder assembly engages the stabilizing rod in a fixed vertical relation to the pedicle screw's head. Accordingly, when multiple polyaxial pedicle screws are situated at substantially different heights along the vertebrae of the spine, certain pedicle screws that are lower than the other pedicle screws are unnecessarily stressed in order to bring their associated rod-holder assemblies toward the stabilizing rod.

In deformity corrective surgeries, pedicle screws are often used to straighten out the spine. More specifically, pedicle screws are used to manipulate the spine, which can involve rotating and translating the vertebrae of the spine in relation to the stabilizing rod. However, a polyaxial screw does not allow de-rotation of a vertebra because the head of the polyaxial pedicle screw is mobile in relation to the attachment of the pedicle screw to the vertebra. More specifically, the polyaxial pedicle screw provides no mechanism to engage the head of the polyaxial pedicle screw in order to rotate or translate the vertebra in relation to the articulating rod.

Moreover, the polyaxial pedicle screw does not provide vertical travel of the rod-holder assembly between the pedicle screw's head and the stabilizing rod for incremental connection to the stabilizing rod at multiple vertical locking positions. Although the polyaxial pedicle screws can be translated along the stabilizing rod (e.g., compression or distraction) to engage or connect to the stabilizing rod, they become much less flexible or useful in pulling or pushing the spine toward the stabilizing rod (e.g., reduction) when translated along the stabilizing rod.

More specifically, a surgeon can place one or more selected polyaxial screws strategically deeper or more superficially into the vertebrae of spine with respect to the stabilizing rod, as may be required for a certain deformity correction. As the stabilizing rod is delivered and tightened to the pedicle screw's associated rod-holder assembly, the pedicle screw will be pushed or more commonly pulled toward the stabilizing rod. However, because the polyaxial pedicle screw provides only one vertical locking position, the deficiencies in the manipulation of the vertebrae in the spine and associated connection to the stabilizing rod are more pronounced, requiring greater surgeon skill and surgical time for the spinal fusion and/or deformity corrective surgery.

SUMMARY

In accordance with an embodiment, a polyaxial vertebral assembly is disclosed. The assembly includes a polyaxial vertebral anchor and an articulating connector. The polyaxial vertebral anchor is configured to penetrate and secure to a vertebra, wherein the polyaxial vetebral anchor includes a spherical head end. The articulating connector includes a base member, a cylindrical extension member, and a common trajectory split lock. The base member has a first axis, and the cylindrical extension member has a second axis that is offset from the first axis. The common trajectory split lock includes a first lock and a second lock. The first lock is configured to engage rigidly the base member of the articulating connector in a selected pivotal configuration to the spherical head end of the polyaxial vertebral anchor along the second axis of the cylindrical extension member, wherein the spherical head end of the polyaxial vertebral anchor is disposed in the base member in the selected pivotal configuration with respect to the first axis of the base member. The second lock is configured to engage rigidly a stabilizing rod at selected configurable height and rotational configuration with respect to the polyaxial vertebral anchor along the second axis of the cylindrical extension member, wherein the pivotal configuration and the height and rotational configuration are independently adjustable along the second axis of the common trajectory split lock.

In accordance with another embodiment, an articulating connector to secure a polyaxial vertebral anchor to a stabilizing rod is disclosed. The articulating connector includes a base member, a cylindrical extension member, and a common trajectory split lock. The base member has a first axis, and the cylindrical extension member has a second axis that is offset from the first axis. The common trajectory split lock includes a first lock and a second lock. The first lock is configured to engage rigidly the base member of the articulating connector in a selected pivotal configuration to a spherical head end of the polyaxial vertebral anchor along the second axis of the cylindrical extension member, wherein the spherical head end of the polyaxial vertebral anchor is disposed in the base member in the selected pivotal configuration with respect to the first axis of the base member. The second lock is configured to engage rigidly a stabilizing rod at selected configurable height and rotational configuration with respect to the polyaxial vertebral anchor along the second axis of the cylindrical extension member, wherein the pivotal configuration and the height and rotational configuration are independently adjustable along the second axis of the common trajectory split lock.

In accordance with further embodiment, a polyaxial vertebral system including at least one stabilizing rod is disclosed. The system includes a first polyaxial vertebral assembly and a second polyaxial assembly.

The first polyaxial vertebral assembly includes a first polyaxial vertebral anchor and a first articulating connector. The first polyaxial vertebral anchor is configured to penetrate and secure to a first vertebra, wherein the first polyaxial vertebral anchor includes a first spherical head end. The first articulating connector includes a first base member, a first cylindrical extension member, and a first common trajectory split lock. The first base member has a first axis, and the first cylindrical extension member has a second axis that is offset from the first axis. The first common trajectory split lock includes a first lock and a second lock. The first lock is configured to engage rigidly the first base member of the first articulating connector in a first selected pivotal configuration to the first spherical head end of the first polyaxial vertebral anchor along the second axis of the first cylindrical extension member, wherein the first spherical head end of the first polyaxial vertebral anchor is disposed in the first base member in the selected pivotal configuration with respect to the first axis of the first base member. The second lock is configured to engage rigidly to the at least one stabilizing rod at first selected configurable height and rotational configuration with respect to the first polyaxial vertebral anchor along the second axis of the first cylindrical extension member.

The second polyaxial vertebral assembly includes a second polyaxial vertebral anchor and a second articulating connector. The second polyaxial vertebal anchor is configured to penetrate and secure to a second vertebra, wherein the second polyaxial vertebral anchor includes a second spherical head end. The second articulating connector includes a second base member, a second base memeber, a second cylindrical extension member, and a second common trajectory split lock. The second base member has a third axis, and the second cylindrical extension member has a forth axis that is offset from the third axis. The second common trajectory split lock includes a third lock and a fourth lock. The third lock is configured to engage rigidly the second base member of the second articulating connector in a second selected pivotal configuration to the second spherical head end of the second polyaxial vertebral anchor along the fourth axis of the second cylindrical extension member, wherein the second spherical head end of the second polyaxial vertebral anchor is disposed in the second base member in the selected pivotal configuration with respect to the third axis of the second base number. The fourth lock is configured to engage rigidly to the at least one stabilizing rod at second selected configurable height and rotational configuration with respect to the polyaxial vertebral anchor along the fourth axis of the second cylindrical extension member.

The first pivotal configuration and the second pivotal configuration, and the first height and rotational configuration and the second height and rotational configuration are independently adjustable along the second axis of the first common trajectory split lock, and along the fourth axis of the second common trajectory split lock, respectively.

These and other purposes, goals and advantages of the present application will become apparent from the following detailed description of example embodiments read in connection with the accompanying drawings.

BRIEF DESCRIPTION OF THE DRAWINGS

Some embodiments are illustrated by way of example and not limitation in the figures of the accompanying drawings in which:

FIG. 1 illustrates a side view of a polyaxial vertebral anchor assembly with vertical adjustment and split lock;

FIGS. 2-4 illustrate various views of a polyaxial vertebral anchor of FIG. 1;

FIGS. 5-11 illustrate various views of a post of FIG. 1;

FIGS. 29-32 illustrate various views of the polyaxial vertebral anchor assembly with vertical adjustment and split lock of FIG. 1;

DETAILED DESCRIPTION

Figure 7:
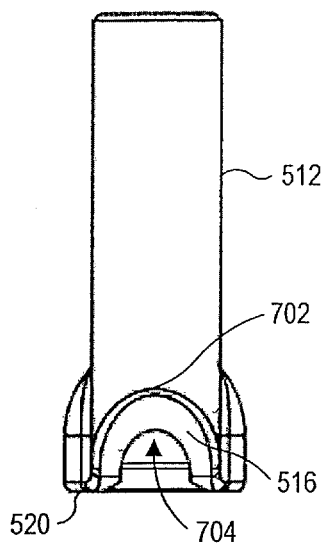

A vertebral anchor assembly with vertical adjustment and split lock, vertebral anchor system and method are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

FIG. 1 illustrates a side view of a polyaxial vertebral anchor assembly with vertical adjustment and split lock 100. The vertebral anchor assembly 100 is configured to provide substantial configurability, including polyaxial articulation with respect to a vertebral anchor, rotational and height articulation with respect to a stabilizing rod, and common trajectory split lock to restrict the foregoing articulation. One or more vertebral anchor assemblies 100 can be utilized in top-loading, side-loading, modular, as well as minimally-invasive surgical approaches.

One or more components of the vertebral anchor assembly 100 can be made of a metal (e.g., titanium, stainless steel, other metals or metal alloys), medical/surgical plastic (e.g., polyethylethylketone (PEEK)), ceramic material, other medically-surgically acceptable material, and combinations of these and/or conventional or later-developed suitable materials that are resilient yet durable to withstand movement of the vertebrae.

The vertebral anchor assembly 100 is suitable for different levels of the spine (e.g., cervical, lumbar, thoracic). The vertebral anchor assembly 100 includes a polyaxial vertebral anchor 102 and articulating connector 104.

The polyaxial vertebral anchor 102 is configured to penetrate and secure to a vertebra. In some embodiments, the polyaxial vertebral anchor 102 is a screw that can penetrate and secure to the vertebra. For example, the vertebral anchor 102 can be a polyaxial pedicle screw that can penetrate and secure to a vertebra through its pedicle. In other embodiments, the polyaxial vertebral anchor 102 can include a polyaxial lamina hook, spinal process hook, transverse process hook, facet screw or bolt, as well as any other polyaxial vertebral anchor that can penetrate and secure to the vertebra.

The articulating connector 104 is configured to provide substantial configurability in a first configuration state, including polyaxial articulation with respect to the polyaxial vertebral anchor 102 and rotational and height articulation with respect to a stabilizing rod 114.

For example, the articulating connector 104 can be snapped onto the polyaxial vertebral anchor 102 after the polyaxial vertebral anchor 102 is placed into the vertebra in a selected trajectory. This enables placement of multiple polyaxial vertebral anchors 102 close to one another. It also allows for one or more articulating connectors 104 and stabilizing rods 114 to be assembled outside of the wound. This is particularly valuable in small direct exposures that are characteristic of the minimally invasive surgical approach.

The articulating connector 104 is further configured to secure rigidly the polyaxial vertebral anchor 102 in a selected relationship with respect to the stabilizing rod 114 in a second configuration state. The articulating connector 104 includes a post 106, saddle 108, washer 110 and nut 112.

The post 106 is configured to snap onto the vertebral anchor 102 and to provide polyaxial articulation (pivotal, rotational) to the articulating connector 104 about the polyaxial vertebral anchor 102. More specifically, the post 106 can pivot (provide angular deflection) about the polyaxial vertebral anchor 102 up to about 40 degrees from an axis that extends along the length of the vertebral anchor 102 and up to about 80 degrees in total. The post 106 can provide 360 degrees of rotation about the axis of the polyaxial vertebral anchor 102.

The post 106 is further configured to engage the saddle 108, washer 110 and nut 112 of the articulating connector 104, as well as the stabilizing rod 114, in one or more locking or engagement locations along the post 106. More specifically, the post 106 can provide vertical travel to the articulating connector 104 along the height of its cylinder (FIG. 5). In some embodiments, vertical travel from about 1.5 mm to about 3.5 mm can be provided. In other embodiments, up to 5.0 mm of vertical travel can be provided. It is noted that vertical travel can be increased or decreased based on the corresponding height of the post 106.

The saddle 108 is configured to slideably engage the post 106. More specifically, the saddle 108 can slide along the post 106 to provide height articulation of the vertebral anchor assembly 100, and more particularly of the articulating connector 104, with respect to the stabilizing rod 114. The saddle 108 is further configured to receive, seat, or engage the stabilizing rod 114.

The washer 110 is configured to engage the saddle 108, confining or securing the stabilizing rod 114 to its seating 116 with respect to the saddle 108. The washer 110 is configured to mitigate unscrewing of the nut 112 from the saddle 108 based on translation of the stabilizing rod 114 with respect to the saddle 108.

The nut 112 is configured to engage the saddle 108 and press the washer 110 to secure the stabilizing rod 114 within its seating 116 with respect to the saddle 108. In turn, the stabilizing rod 114 is configured to engage the post 106 through the saddle 108, fixating rigidly the vertical height of the vertebral anchor assembly 100, and more particularly of the articulating connector 104, with respect to the stabilizing rod 114.

In some embodiments, the washer 110 can be omitted and the nut 112 can confine and engage the stabilizing rod 114 into its seating 116 with respect to the saddle 108, which in turn can cause the stabilizing rod 114 to engage the post 106 through the saddle 108, fixating rigidly the vertical height of the vertebral anchor assembly 100, and more particularly of the articulating connector 104, with respect to the stabilizing rod 114.

FIG. 2 illustrates a side view of the polyaxial vertebral anchor 102 of FIG. 1. The polyaxial vertebral anchor 102 includes a vertebral engagement end 202, connecting head end 210 and neck 212.

The polyaxial vertebral anchor 102 can have an overall height from about 40.0 mm to about 60.0 mm. The height of the engagement end 202 can be from about 12.0 mm to about 55.0 mm; the connecting head end 210 from about 3.0 mm to about 5.0 mm; and the neck 212 from about 2.0 mm to about 4.0 mm. The respective heights of the vertebral engagement end 202, connecting head end 210 and a neck 212 can be adjusted based on the level of the spine (e.g., cervical, lumbar, thoracic) and the patient.

A diameter of the vertebral engagement end 202 (including the external thread) can be from about 3.5 mm to about 9.5 mm. A diameter of the connecting head end 210 can be from about 3.0 mm to about 5.0 mm. A diameter of the neck 212 can be from about 2.0 mm to about 4.0 mm.

The foregoing heights and diameters can be varied based on level of the spine (e.g., cervical, lumbar, thoracic) into which the polyaxial vertebral anchor 102 is to be engaged. As illustrated in FIG. 2, the neck 212 has a smaller diameter than the respective diameters of the vertebral engagement end 202 and connecting head end 210.

The vertebral engagement end 202 is configured to penetrate and secure to a vertebra. The vertebral engagement end 202 includes a round shaft 204, external thread 206 and tip 208. The thread 206 is provided along a portion of the shaft 204 below the connecting head end 210 and neck 212, such that the polyaxial vertebral anchor 102 can engage a vertebra and yet allow the post 106 of the articulating connector 104 to articulate (rotate and pivot) with respect to polyaxial vertebral anchor 102.

It is noted that different thread types can be implemented as the external thread 206 in the vertebral engagement end 202 for various mechanical advantages, such as a standard thread, double thread, tapered core diameter thread, dual cortical-cancellous thread, as well any other medically/surgically appropriate thread.

The tip 208 tapers from a terminal end of the shaft 204 and is configured to enable the screw 102 to penetrate the vertebra. The thread 206 and tip 208 can be self-cutting and/or the vertebra can be pre-drilled. The tip 208 can include a guide wire opening 218 configured to receive a guide wire (not shown) that can guide the polyaxial vertebral anchor 102 to an appropriate location of the vertebra. The guide wire opening 218 can have a diameter from about 1.0 mm to about 2.0 mm.

The connecting head end 210 is spherical and is configured to engage the post 106, such that the post 106 can articulate (rotate and pivot) with respect to the polyaxial vertebral anchor 102 in a first configuration, and such that the post 106 can lock or engage rigidly in a selected articulation with respect to the polyaxial vertebral anchor 102 in a second configuration, as will be described in greater detail herein.

The neck 212 includes sloping chamfered surfaces 214, 216 configured to transition the vertebral engagement end 202 to the connecting head end 210. The neck 212 is configured to allow the post 106 to articulate (rotate and pivot) with respect to the polyaxial vertebral anchor 102 via the connecting head end 210.

FIG. 3 illustrates a perspective view of the polyaxial vertebral anchor 102 of FIG. 1. For the sake of simplicity and brevity, the external thread 206 is not shown along the shaft 204.

The connecting head end 210 of the polyaxial vertebral anchor 102 further includes a driver engagement opening 302 configured to engage a driver tool (not shown). The driver engagement opening 302 can have a diameter of 2.0 mm to about 3.0 mm. Other diameters for the driver engagement opening 302 are possible based on the diameter of the connecting head end 210 and the driver tool.

The driver tool (e.g., screwdriver) can engage the driver engagement opening 302 and can further rotate the polyaxial vertebral anchor 102 to penetrate and engage a vertebra. The diameter of the driver engagement opening 302 can be defined by truncating the connecting head end 210 along a plane that is approximately perpendicular to an axis that extends along the height of the polyaxial vertebral anchor 102, as illustrated in greater detail in FIG. 4.

FIG. 4 illustrates a top view of the polyaxial vertebral anchor 102 of FIG. 1. The top of the polyaxial vertebral anchor 102 can be defined by a plane that is approximately perpendicular to an axis that extends along the height of the polyaxial vertebral anchor 102.

The driver engagement opening 302 includes one or more recesses 402 that are configured to engage reciprocal extensions of the driver tool that can be used to drive (rotate) the polyaxial vertebral anchor 102 into a vertebra to be engaged. Similarly, the extensions of driver tool can engage the reciprocal recesses 402 to rotate (unscrew) the polyaxial vertebral anchor 102 from the engaged vertebra.

The recesses 402 can be disposed at various locations about the driver engagement opening 302. In some embodiments as illustrated in FIG. 4, six recesses 402 are disposed about the periphery of the driver engagement opening 302. In other embodiments, fewer recesses 402 can be provided. For these other embodiments, reciprocal extensions in the driver tool can be provided to drive (screw, unscrew) the polyaxial vertebral anchor 102 in relation to the vertebra.

Various recesses 402 can be provided to form driver engagement openings 302 that can be modified for corresponding driver tools, such as phillips, square, star, hex, slotted, as well as other appropriate medical/surgical driver tools.

As further illustrated in FIG. 4, the polyaxial vertebral anchor 102 also includes a cannulated opening 404 that extends through the height of the polyaxial vertebral anchor 102 to the opening 218 at the tip 208, as illustrated in FIG. 2. The cannulated opening 404 is configured to receive the guide wire received through the opening 218 to guide the polyaxial vertebral anchor 102 to an appropriate location of the vertebra.

FIG. 5 illustrates a side view of the post 106 of FIG. 1.

As described hereinabove, the post 106 is configured to provide polyaxial articulation to the articulating connector 104 about the connecting head end 210 of vertebral anchor 102 in a first configuration. The connecting head end 210 can be engaged or locked via a setscrew (FIG. 12) in a selected trajectory with respect to the post 106 in a second configuration.

The post 106 is further configured to slideably engage the saddle 108, washer 110 and nut 112 of the articulating connector 104, as well as the stabilizing rod 114, in one or more slideable locations along the height of a the post 106 in a third configuration. The post 106 is further configured to engage or lock rigidly with respect to the saddle 108, washer 110 and nut 112 of the articulating connector 104, as well as the stabilizing rod 114, at a selected location along the height of the post 106 in a fourth configuration.

The post 106 can have a height from about 20.0 mm to about 40.0 mm, depth (front to back) from about 12.0 mm to about 14.0 mm, and width (side to side) from about 10.0 mm to about 11.0 mm. Alternate height, depth and width dimensions are possible based on the level of the spine (e.g., cervical, lumbar, thoracic) and the patient.

The post 106 includes a base member 502 and an extension member 510. The base member 502 is defined by a sphere 504 and cylinder (tube) 506. The base member 502 has an axis, and diameters of the sphere 504 and cylinder 506 of the base member 502 can be from about 10.0 mm to about 11.0 mm. The cylinder 506 can include a chamfer 508. The base member 502 transitions smoothly between the sphere 504, cylinder 506 and chamfer 508.

The extension member 510 is defined by a cylinder (tube) 512 and an arch 516. The cylinder 512 can include a chamfer 514. The cylinder 512 has an axis and can have an external diameter from about 7.0 mm to about 8.0 mm. Alternate dimensions are possible based on dimensions of other components of the articulating connector 104. The arch 516 can be oval-shaped (or ellipse-shaped) and extends from side to side of the post 106 (FIG. 7).

The sphere 504 and cylinder 506 of the base member 502 can transition smoothly to the cylinder 512 of extension member 510 via transition 518, and the chamfer 508 of the base member 502 can transition smoothly to the arch 516 of the extension member 510 via arcuate chamfer 520.

FIG. 6 illustrates a front view of the post 106 of FIG. 1. The cylinder 512 of the extension member 510 includes a channel 602 and planar rails 604, 606, which extend along the height of the extension member 510. The contour of the channel 602 can be defined along the cylinder 512 with a circular shape that has an axis and a diameter.

As will be described in greater detail below, the diameter of the circular shape that defines the channel 602 approximates the diameter of a hole (FIG. 8) through the top of the base member 502. These diameters are approximately coaxial with respect to the axis of the base member 502. The channel 602 is thus configured to provide line-of-sight (straight) access for a driver tool to engage vertebral anchor 102 along the extension member 510 and through the hole of the base member 502, e.g., such that the extension member 510 does not block a portion of the hole in the base member 502.

The rails 604, 606 are approximately coplanar and extend along the height of the extension member 510. The rails 604, 606 are configured to engage the stabilizing rod 114 through the saddle 108 at a selected engagement location along the extension member 510 of the post 106 when the nut 112 depresses the stabilizing rod 114 into the saddle 108.

FIG. 7 illustrates a back view of the post 106 of FIG. 1. The arch 516 transitions smoothly to the cylinder 512 and to the arcuate chamfer 520 via a chamfer 702.

The post 106 includes an opening 704 that is configured to enable insertion of the vertebral anchor 102 into the post 106 and articulation of the post 106 with respect to the vertebral anchor 102.

The arch 516 provides a greater polyaxial (pivotal) articulation to the articulating connector 104 about the polyaxial vertebral anchor 102. More specifically, the post 106 can pivot (provide angular deflection) about the polyaxial vertebral anchor 102 up to about 80 degrees from an axis that extends along the length of the vertebral anchor 102 through the arch 516 and up to about 120 degrees in total.

Figure 8:
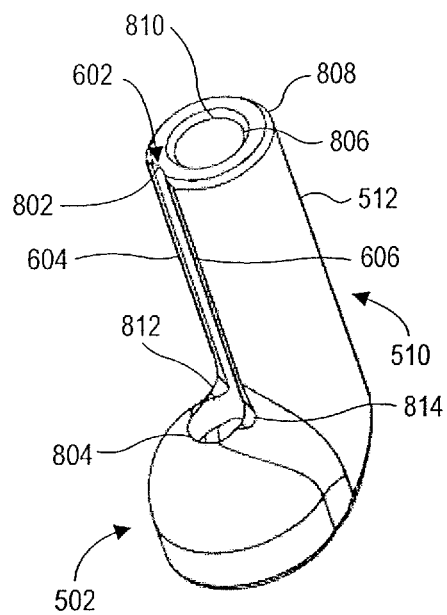

FIG. 8 illustrates a perspective view of the post 106 of FIG. 1. The post 106 includes through holes 804 and 806.

The through hole 804 extends through to the opening 704. The hole 804 is configured to enable a driver tool to engage and drive (screw and unscrew) the vertebral anchor 102 into a vertebra through the hole 804 along channel 602 of the cylinder 512. The hole 804 can have a diameter from about 2.0 mm to about 3.0 mm. Alternative dimensions of the hole 804 are possible.

A diameter of a circular shape 802 that defines the channel 602 approximates the diameter of the hole 804 through the top of the base member 502. The circular shape 802 and the hole 804 are approximately coaxial with respect to the axis of the base member 502. Accordingly, the channel 602 provides line-of-sight access for a driver tool to engage vertebral anchor 102 along the cylinder 512 of extension member 510 through the hole 804, e.g., such that the extension member 510 does not block a portion of the hole 804 in the base member 502.

The through hole 806 extends through to the opening 704. The hole 806 is configured to enable introduction of a setscrew (FIG. 12) and diver tool (not shown) through the cylinder 512 and rigid engagement via the setscrew of the post 106 with respect to the vertebral anchor 102. The hole 806 can have a diameter (including internal thread) of about 3.0 mm to about 5.0 mm.

Figure 12:
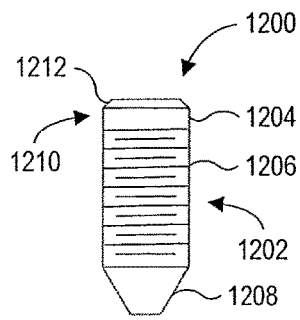
FIGS. 12-14 illustrate various views of a setscrew used in FIG. 1.

The through hole 806 is further configured to receive an extension tube for certain surgical approaches. The extension tube can have a similar (or the same) outer diameter as the cylinder 512, can include an internal through hole along the height of the extension tube and can further include a terminal connector configured to friction-fit the opening 806, such that the cylinder 512 can be extended. A driver tool (e.g., screwdriver), can be inserted via the through hole of the extension tube and can be used to rotate the setscrew (FIG. 12). One or more of the other components of the articulating connector 104, as well as articulating rod 114 (in some embodiments), can be slideably engaged to the cylinder 512 via its extension tube.

For example, a combination of the saddle 108, washer 110, nut 112 and stabilizing rod 114 can be engaged to the cylinder 512 of the post 106 via the aforementioned extension tube. It is noted that the nut 112 does not tightly secure the stabilizing rod 114, such that the combination of components can slideably engage the cylinder 512 of the post 106. In some embodiments, the washer 110 can be omitted and the saddle 108, nut 112 and stabilizing rod 114 can be engaged. As another example, a combination of the saddle 108 and nut 112 can slideably engage the cylinder 512 of the post 106. Other combinations are possible.

The cylinder 512 can include an outside chamfer 808 and an inside chamfer 810. The outside chamfer 808 can facilitate engagement of the saddle 108 and washer 110 onto cylinder 512 of the post 106, while the inside chamfer 810 can facilitate insertion of the setscrew (FIG. 12) through the cylinder 512 of the post 106 and rotation of the setscrew to rigidly engage the vertebral anchor 102 with respect to the post 106. The inner chamfer can further facilitate engagement of the aforementioned extension tube to the cylinder 512 of the post 106.

Recesses 812, 814 can be provided in the base member 502, at the foot of the rails 604, 606 and about the hole 804. The recesses 812, 814 allow the saddle 108 to be seated as low as possible along the post 106, providing increased height articulation to the articulating connector 104.

Figure 9:
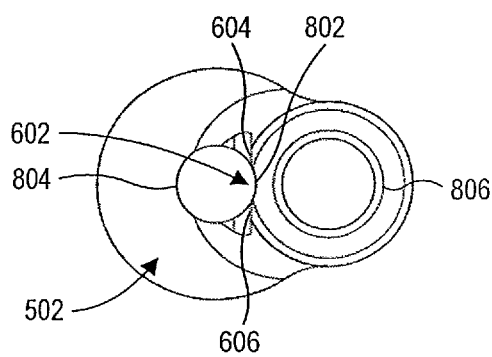

FIG. 9 illustrates a top view of the post 106 of FIG. 1.

The diameter of a circular shape 802 that defines the channel 602 approximates the diameter of the through hole 804 through the top of the base member 502. As illustrated, the circular shape 802 and the through hole 804 are approximately coaxial with respect to the axis of the base member 502, allowing unimpeded engagement and rotation of the vertebral anchor 102.

As further illustrated in FIG. 9, rails 604, 606 are approximately co-planar along a plane that bisects the post 106 approximately in half.

Figure 10:
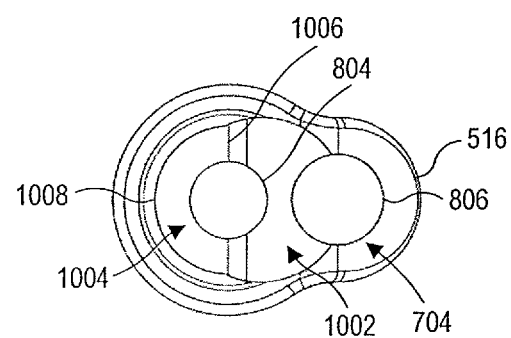

FIG. 10 illustrates a bottom view of the post 106 of FIG. 1. The opening 704 in the post 106 enables insertion of the vertebral anchor 102 into the post 106 and articulation of the post 106 with respect to the vertebral anchor 102. The opening 704 includes a first recess 1002, second recess 1004, ramp 1006 and lip 1008.

As described below in greater detail, two-stage insertion—via first recess 1002 and second recess 1004—provides simplicity and accuracy for inserting the connecting head end 210 into articulating engagement with respect to the post 106.

The first recess 1002 is configured to receive the connecting head end 210 of the vertebral anchor 102 in one or more trajectories with respect to the post 106 through the opening 704. The arch 516 affords additional trajectories for insertion of the connecting head end 210 into the post 106. Because the operative wound and the muscle of the patient can restrict the trajectory for the receipt of the connecting head end 210, the arch 516 provides additional oblique (angular) trajectories for the receipt of the connecting head end 210 into the post 106.

The first recess 1002 has an approximately spherical shape that is larger than that of the connecting head end 210 of the vertebral anchor 102 in order to facilitate easier insertion of the connecting head end 210 at various trajectories with respect to the post 106. The connecting head end 210 can be received into the first recess 1002 approximately inline or at an oblique (angular) trajectory with respect to the extension member 510 of the post 106 to facilitate insertion of the connecting head end 210 during various surgical procedures (e.g., lateral surgical procedure, open fusion surgical procedure, minimally invasive, as well as other surgical procedures).

Moreover, the first recess 1002 extends or transitions into the second recess 1004 via the ramp 1006. The second recess 1004 has an approximately spherical shape that is smaller than the first recess 1002 and that approximates that of the connecting head end 210 of the vertebral anchor 102 in order to facilitate articulation of the post 106 with respect to the connecting head end 210.

The ramp 1006 is configured to facilitate smooth insertion of the vertebral anchor 102 from the first recess 1002 into the smaller second recess 1004.

The lip 1008 extends about at least a portion of the second recess 1004. The lip 1008 fits precisely over the spherical connecting head end 210 and is configured to retain or secure the connecting head end 210 of the vertebral anchor 102 in the second recess 1004, such that the post 106 can articulate with respect to the connecting head end 210 of the vertebral anchor 102.

Figure 11:
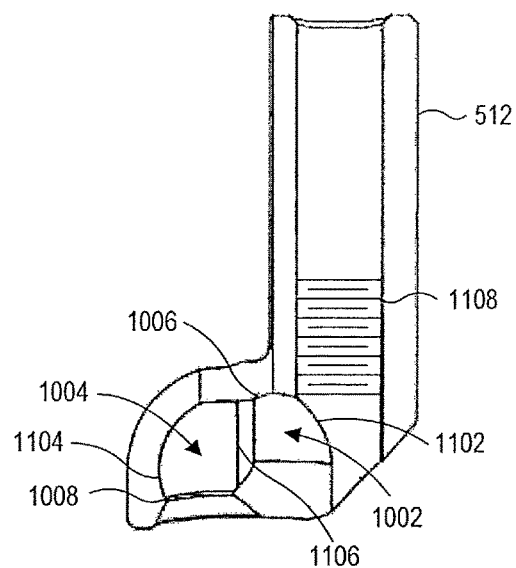

FIG. 11 illustrates a cross-sectional side view of the post 106 of FIG. 1. As illustrated, the first recess 1002 has an approximately spherical shape 1102 that is larger than that of the connecting head end 210 of the vertebral anchor 102 in order to facilitate insertion into the post 106.

The second recess 1004 has an approximately spherical shape 1104 that approximates that of the connecting head end 210 of the vertebral anchor 102 in order to facilitate articulation of the post 106 with respect to the connecting head end 210. The lip 1008 fits precisely over a portion of the spherical connecting head end 210 (e.g., about half of the connecting head end 210) and retains the connecting head end 210 of the vertebral anchor 102 in the second recess 1004.

A remaining portion of the spherical connecting head end 210 (e.g., about half of the connecting head end 210) protrudes or extends into the first recess 1002, such that a setscrew (FIG. 12) can engage the connecting head end 210 and press it into at least a portion of the second recess 1004, securing rigidly the vertebral anchor 102 in a selected articulated configuration with respect to the post 106.

As further illustrated in FIG. 11, the post 106 also includes a second ramp 1106 and an internal thread 1108.

The second ramp 1106 is configured to facilitate insertion of the vertebral anchor 102 from the first recess 1002 into the smaller second recess 1004.

The internal thread 1108 is provided along a lower portion of the cylinder 512 and extends to the intersection with the first recess 1002, such that a setscrew (FIG. 12) can engage the connecting head end 210 and press it into at least a portion of the second recess 1004, securing rigidly the vertebral anchor 102 in a selected articulated configuration with respect to the post 106. Different types of internal thread 1108 can be employed for various mechanical advantages, such as a standard thread, double thread, tapered core diameter thread, as well any other medically/surgically appropriate thread.

The setscrew (FIG. 12) can be preloaded, rotatably engaging the internal thread 1108. To allow articulation of the post 106 with respect to the connecting head end 210 of the vertebral anchor 102, the setscrew can protrude partially into the first recess 1002 to provide sufficient pressure not only to retain the connecting head end 210 in the second opening 1004 but also to enable articulation of the post 106 with respect to the vertebral anchor 102.

To restrict articulation of the post 106 with respect to the vertebral anchor 102, the setscrew is rotated/advanced further into the cylinder 512, such that the setscrew engages rigidly the connecting head end 210 and presses it into at least a portion of the second recess 1004 to secure rigidly the vertebral anchor 102 in a selected articulated configuration with respect to the post 106.

FIG. 12 illustrates a side view of an example setscrew 1200 used in FIG. 1. The setscrew 1200 is configured to engage the connecting head end 210 such that the post 106 can articulate in relation to the connecting head end 210. The setscrew 1200 is further configured to press the connecting head end 210 into at least a portion of the second recess 1004 (FIG. 11), securing rigidly the vertebral anchor 102 in a selected articulated configuration with respect to the post 106.

The setscrew 1200 can have an overall height from about 12.0 mm to about 14.0 mm. The setscrew can have a diameter (including the external thread) of about 4.0 mm to about 5.0 mm. Alternative dimensions of the setscrew 1200 that correspond to the dimensions of the thread 1108 in the post 106 are of course possible.

The setscrew 1200 includes a body 1202 and head 1210. The body 1202 includes a shaft 1204, external thread 1206 and tip 1208. The thread 1206 is provided along at least a portion of the shaft 1204 below the head 1210, such that the setscrew 1200 can engage the internal thread 1108 in the cylinder 512 of the post 106. It is noted that while different thread types can be implemented as the external thread 1206 for various mechanical advantages, the thread 1206 should match the internal thread 1108 in the cylinder 512 of the post 106.

The tip 1208 tapers from the shaft 1202 and is configured to enable the setscrew 1200 to engage the connecting head end 210 of the vertebral anchor 102 in an articulable relationship to the post 106, and further to press connecting head end 210 into at least a portion of the second recess 1004 (FIG. 11), securing or locking rigidly the vertebral anchor 102 in a selected articulated configuration with respect to the post 106.

The head 1210 can include a sloping chamfered surface 1212. As will be described in greater detail below, the head 1210 is configured to engage a driver tool (not shown) to rotate the setscrew 1200 in the cylinder 512 of the post 106.

Figure 13:
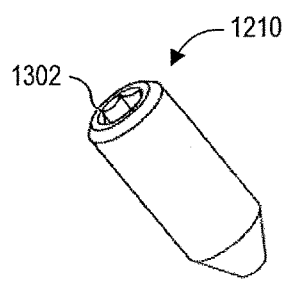

FIG. 13 illustrates a perspective view of the setscrew 1200 of FIG. 12. For the sake of simplicity and brevity, the external thread 1206 is not shown along the shaft 1204. The head 1210 of the setscrew 1200 includes a driver engagement opening 1302 configured to engage a driver tool (not shown).

The driver engagement opening 1302 can have a diameter from about 2.0 mm to about 3.0 mm. Other diameters for driver engagement opening 1302 are possible based on the diameter of the head 1210 and the driver tool.

The driver tool (e.g., screwdriver) can engage the driver engagement opening 1302 and can further rotate (screw/unscrew) the setscrew 1200 via the engagement opening 1302 with respect to the cylinder 512 of the post 106, providing articulable or rigid connection of the post 106 to the connecting head end 210 of the vertebral anchor 102.

Figure 14:
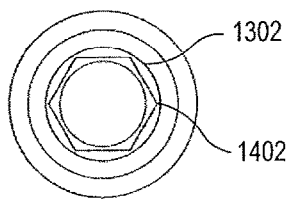

FIG. 14 illustrates a top view of an example setscrew 1200 of FIG. 12. The top of the setscrew 1200 can be defined by plane that is approximately perpendicular to an axis that extends along the height of the setscrew 1200.

The driver engagement opening 1302 includes one or more recesses 1402 that are configured to engage reciprocal extension(s) of a driver tool that can be used to rotate (screw/unscrew) the setscrew 1200 with respect to the cylinder 512 of the post 106.

The recesses 1402 can be disposed at various locations about the driver engagement opening 1302. In some embodiments as illustrated in FIG. 14, one hex-shaped recess 1402 is disposed about the driver engagement opening 1302. In other embodiments, various recesses 1402 can be provided to form driver engagement openings 1302 that can be modified for corresponding driver tools, such as phillips, square, hex, star, slotted, as well as other driver tools.

Figure 15:
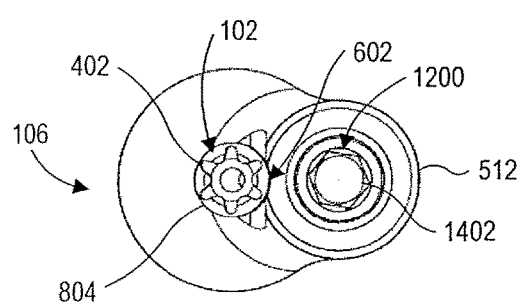
FIGS. 15 and 16 illustrate various views of the engagement of a vertebral anchor and a post via a setscrew in a group of components.

FIG. 15 illustrates a top view of the engagement of the vertebral anchor 102 and the post 106 via the setscrew 1200 in a group of components. The components of the vertebral anchor assembly 100 can be implanted individually or assembled in various groups or combinations before or during implantation.

For example, the vertebral anchor 102 can first be secured to a vertebra, followed by the assembled articulating connector 104 and the stabilizing rod 114, which can be tightened or secured to the vertebral anchor 102 in rigid configuration with the setscrew 1200 and nut 112, respectively.

As another example, the vertebral anchor 102, post 106 and setscrew 1200 can be assembled into a group or combination shown in FIG. 15. In this case, the setscrew 1200 can secure the post 106 semi-rigidly to the vertebral anchor 102 to provide freedom of articulation (pivoting and rotation) of the post 16 with respect to the vertebral anchor 102.

The group or combination (vertebral anchor 102, post 106 and setscrew 1200) can then be secured to a vertebra of the patient by engaging a driver tool via the through hole 402 and channel 602, and then securing the vertebral anchor 102 to the vertebra. The post 106 can then be articulated (rotated and/or pivoted) as may be required in relation to the vertebral anchor 102 and then rigidly secured to the vertebral anchor 102 by engaging a driver tool via recesses 1402 and rotating the setscrew 1200 into the cylinder 512 of post 106.

Figure 16:
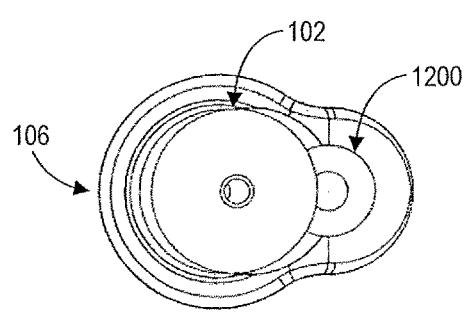

FIG. 16 illustrates a bottom view of the engagement of the vertebral anchor 102 and the post 106 via the setscrew 1200 in the group or combination of FIG. 15.

As illustrated, the vertebral anchor 102, post 106 and setscrew 1200 can be secured rigidly or semi-rigidly with respect to the post 106 in an inline (non-pivoted) or articulated (pivoted) configuration and a rotational configuration.

The rotational and/or pivotal configuration can be adjusted by loosening the setscrew 1200 to allow the post 106 to rotate and pivot about the vertebral anchor 102. Once a pivotal configuration and/or rotational configuration are/is selected, the setscrew 1200 can be tightened, securing the post 106 rigidly to the vertebral anchor 102.

Figure 17:
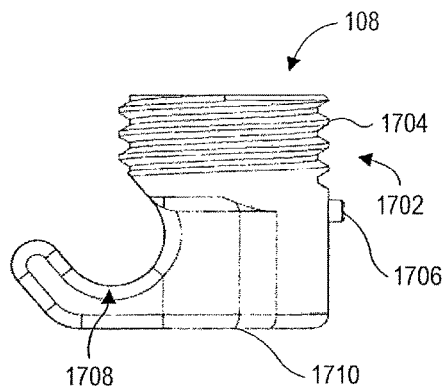
FIGS. 17-22 illustrate various views of a saddle of FIG. 1.

FIG. 17 illustrates a side view of the saddle 108 of FIG. 1. The saddle 108 is configured to slideably engage the post 106 and to receive the stabilizing rod 114.

The saddle 108 can be from about 14.0 mm to about 16.0 mm deep (front to back), from about 10.0 mm to about 12.5 mm wide (side to side), and from about 10.0 mm to about 11.0 mm high. Alternate dimensions can be selected based on the dimensions of the other components in the connector 104, which can be based on different levels of the spine (e.g., cervical, lumbar, thoracic) and the patient.

The saddle 108 includes a cylindrical (tubular) body 1702 and seat 1708. The cylindrical body 1702 has an axis and includes an opening (FIG. 19), external thread 1704 and stop 1706. The thread 1704 is configured to receive in rotatable engagement the nut 112. The stop 1706 is configured to engage a slot in the washer 110 (FIG. 24), such that the washer 110 does not rotate in relation to the saddle 108.

The seat 1708 is below the thread 1704. Further, the seat 1708 intersects the opening (FIG. 19) of cylindrical body 1702 and projects in a curvilinear (arcuate) configuration away from the body 1702. More specifically, the seat 1708 is configured to receive the stabilizing rod 114. A chamfer 1710 can be provided along the contours of the seat 1708.

The curvature of the seat 1708 approximates the curvature of the stabilizing rod 114, such that the stabilizing rod 114 can be disposed precisely in the seat 1708. In some embodiments, the seat 1708 can be wider (side to side) than an external diameter of cylindrical body 1702 to provide a wider seat 1708 for the stabilizing rod 114. For example, the width can serve to provide structural integrity such that the seat 1708 does not deform in relation to post 106, when in operation, the articulating rod 114 applies various forces to the articulating connector 104. In other embodiments, the seat 1708 can have a width (side to side) that is approximately the diameter of the cylindrical body 1702 to reduce the hardware profile of the articulating connector 104. In various alternate embodiments, the seat 1708 can be wider or narrower than the diameter of the cylindrical body 1702.

The nut 112 can press the stabilizing rod 114—for example, via washer 110 (if used)—into the seat 1708 such that the stabilizing rod 114 interferes with or projects into the opening (FIG. 19) of the cylindrical body 1702 via an opening (FIG. 18) in the saddle 108.

Figure 18:
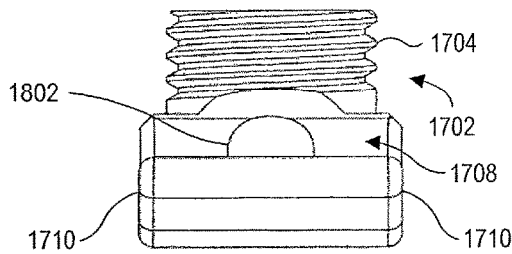

FIG. 18 illustrates a front view of the saddle 108 of FIG. 1. As illustrated, the seat 1708 is configured to intersect the cylindrical body 1702 such that an opening 1802 is formed in the seat 1708 that is in communication with the opening (FIG. 19) of the cylindrical body 1702.

The opening 1802 can be generally circular. In some embodiments, the opening 1802 can have a diameter from about 5.0 mm to about 6.0 mm. Alternate shapes and dimension of the opening 1802 are possible based on various dimensions of the other components in the articulating connector 104.

More specifically, the diameter (or width side to side) of the opening 1802 is sufficient to enable the planar rails 604, 606 of the post 106 (FIG. 6) to interfere with or project into the seat 1708 and the stabilizing rod 114 to engage the planar rails 604, 606 when depressed by the nut 112 into the seat 1708, such that vertical travel along post 106 is restricted and the components (post 106, saddle 108, washer 110 and nut 112) of the connector 104 are secured rigidly with respect to one another and with respect to the stabilizing rod 114.

Figure 19:
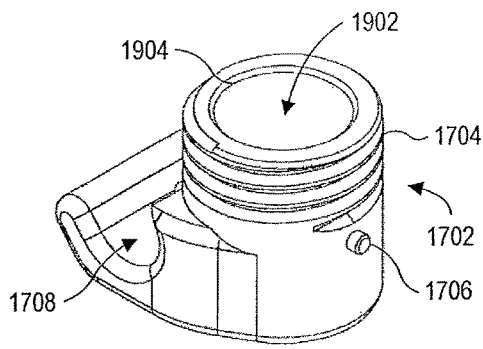

FIG. 19 illustrates a perspective view of the saddle 108 of FIG. 1. The cylindrical body 1702 of the saddle 108 includes a through opening 1902 that is configured to slideably engage the post 106.

The opening 1902 can have a diameter from about 7.0 mm to about 8.0 mm. Alternate diameters of the opening 1902 can be used based on the external diameter of the post 106, such that the saddle 108 can slideably engage the post 106 along the axis of the cylinder 512. An interior chamfer 1904 can be provided about the opening 1902 of cylindrical body 1702.

Figure 20:
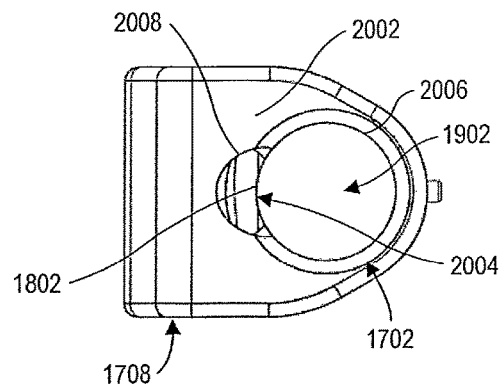

FIG. 20 illustrates a bottom view of the saddle 108 of FIG. 1. The saddle 108 can have a planar bottom 2002 that extends or transitions smoothly to the curvilinear seat 1708.

As illustrated, the opening 1902 of the cylindrical body 1702 intersects the opening 1802 at 2004. A chamfer 2006 can be provided about the opening 1902 extending from the bottom 2002 of the saddle 108 to facilitate slideable engagement of the saddle 108 with respect to the post 106.

Figure 21:
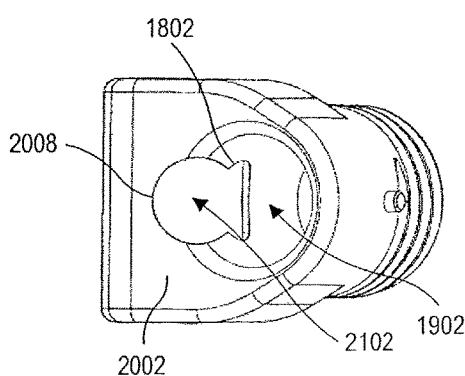

An opening 2008 can be formed in the bottom 2002 through the cylindrical body 1702 and the seat 1708 (FIG. 21). The opening 2008 can be circular and can have a diameter from about 5.0 mm to about 6.0 mm. Alternate dimensions are possible.

The openings 1802, 2008 can be lined up or approximated with the opening 804 and channel 602 in the post 106 (FIG. 8) such that a driver tool can extend through the openings 1802, 2008, 804 and the channel 602 to drive (rotate) the vertebral anchor 102.

FIG. 21 illustrates a bottom perspective view of the saddle 108 of FIG. 1. As illustrated, the opening 2008 through the bottom 2002 is at angle with respect to the opening 1802 through the seat 1708 (e.g., 45 degrees). The angle can be adjusted.

The combination of the openings 1802, 2008 creates an expanded opening 2102 configured to enable a driver tool to extend through the expanded opening 2102, opening 802 and channel 602 in the post 106 to drive (rotate) the vertebral anchor 102.

Figure 22:
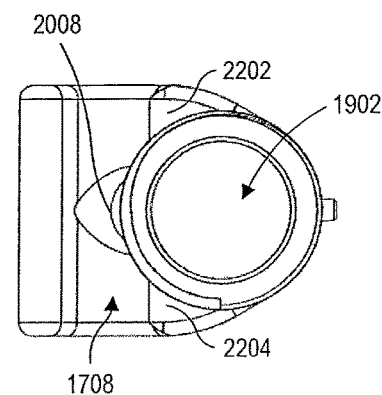

FIG. 22 illustrates a top view of the saddle 108 of FIG. 1. The saddle 108 includes surfaces or stops 2202, 2204 that are configured to mate with the washer 110, such that the washer 110 can be disposed in a planar configuration in relation to the saddle 108. In some embodiments, the washer 110 can be omitted and the nut 112 can mate with the surfaces or stops 2202, 2204 of the saddle 108, such that the nut 112 can be disposed in a planar configuration in relation to the saddle 108.

Figure 23:
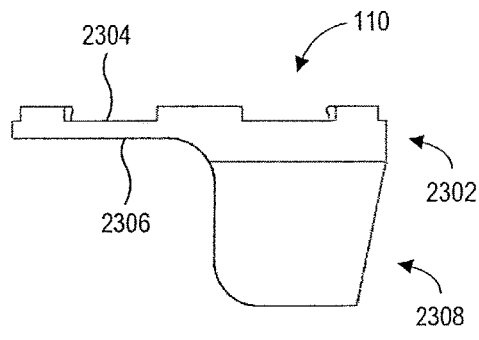
FIGS. 23-25 illustrate various views of a washer of FIG. 1.

FIG. 23 illustrates a side view of the washer 110 of FIG. 1. The washer 110 includes a ring 2302 and back 2308.

The ring 2302 includes a central opening (FIG. 25), seat 2304 and engagement surface 2306. The ring 2302 of the washer 110 slideably engages the cylindrical body 1702 of the saddle 108 via its central opening. The seat 2304 is configured to receive the nut 112 in a planar configuration.

The engagement surface 2306 is configured to mate with stops 2202, 2004 of the saddle 108 (FIG. 22), such that the washer 110 can be disposed in a planar configuration with respect to the saddle 108. The engagement surface 2306 is further configured to engage and press the stabilizing rod 114 into the seat 1708 of the saddle 108 when pressed by the nut 112, as described in greater detail herein.

The back 2308 extends below the ring 2302 and around about a portion (e.g., half) of the perimeter of the ring 2302. The outer surface of the back 2308 slopes toward the interior of the ring 2302 for smaller and more tapered profile. It should be noted that the inner surface of the back 2308 is generally non-sloping toward the interior of the ring 2302 (e.g., having a similar configuration or curvature to the saddle 108), such that the washer 110 can fit precisely over the saddle 108.

Figure 24:
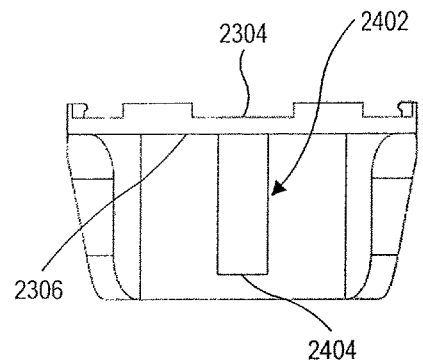

FIG. 24 illustrates a front view of the washer 110 of FIG. 1. The washer 110 further includes a guide channel 2402 that extends from and through the seat 2304 of the ring 2302 along a portion of the back 2308 until a terminal end 2404 of the guide channel 2402.

The guide channel 2402 is configured to engage the stop 1706 of the saddle 108 (FIG. 17) and to provide for slideable insertion of the washer 110 in an appropriate orientation with respect to the saddle 108 in which the stop 1706 rides along the guide channel 2402.

The terminal end 2404 is configured to stop disengagement of the washer 110 from the saddle 108 when the terminal end 2406 of the guide channel 2402 engages the stop 1706 of the saddle 108.

Figure 25:
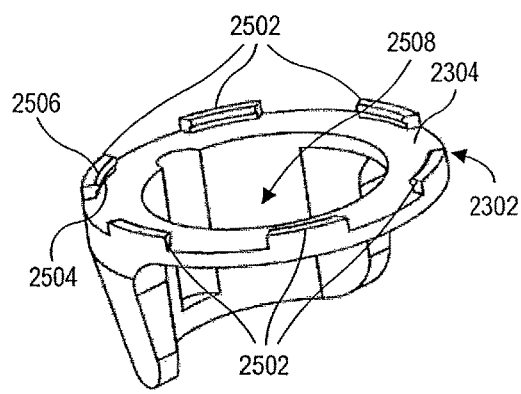

FIG. 25 illustrates a perspective view of the washer 110 of FIG. 1. A plurality of engagement projections 2502 extend from the seat 2304 about the periphery of the washer 110.

The engagement projections 2502 include lips 2504 and chamfers 2506. The engagement projections 2502 are configured to deflect outward as the nut 112 is depressed into the seat 2304 via chamfers 2506 and to engage a lip (FIG. 27) of the nut 112 in a friction-fit engagement once the nut 112 is disposed in the seat 2304 (FIG. 31). The friction-fit engagement reduces the possibility that the nut 112 can be unscrewed from the saddle 108 in the operation of the vertebral anchor assembly 100 of FIG. 1.

The ring 2302 includes a central opening 2508 configured to enable the washer 110 to slideably engage the cylindrical body 1702 of the saddle 108 via the central opening 2508. The diameter of the opening 2508 can be from about 10.0 mm to about 11.0 mm to slideably engage the saddle 108. The outer diameter of the seat 2404 can be from about 16.0 mm to 17.0 mm to engage the nut 112. Alternative dimensions are possible.

Figure 26:
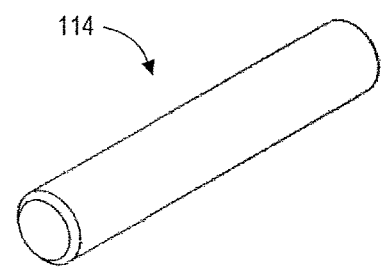
FIG. 26 illustrates a stabilizing rod of FIG. 1.

FIG. 26 illustrates a perspective view of the stabilizing rod 114 of FIG. 1.

The stabilizing rod 114 is configured to be disposed and secured rigidly in the saddle 108 via the washer 110 when pressed by the nut 112. In some embodiments omitting the washer 110, the stabilizing rod 114 can be the pressed into the saddle 108 by the nut 112. The stabilizing rod 114 can have a diameter from about 4.0 mm to about 6.0 mm.

While the stabilizing rod 114 is illustrated as having generally uniform diameter, shape and/or configuration, it should be noted that the stabilizing rod 114 could be fashioned to have variable diameters, lengths, shapes and configurations depending on the vertebrae in the spine to be spanned by the vertebral anchors 100. For example, the stabilizing rod 114 can be straight, curvilinear (arc shaped), or even custom-shaped. There are existing tools to customize the articulating rod 114 intraoperatively. Alternate dimensions can be used based on the dimensions of the other components in the connector 104, which can be based on different levels of the spine (e.g., cervical, lumbar, thoracic) and the patient.

Depending on the surgical application, the stabilizing rod 114 can be made of a metal (e.g., titanium, stainless steel, other metals or metal alloys), a heavy impact plastic (e.g., polyethylethylketone (PEEK)), or a flexible plastic (e.g., polycarbonated urethane). For certain surgical applications, the stabilizing rod 114 can also incorporate a spring (not shown). Conventional or yet to be developed stabilizing rods can be used with the vertebral anchor assemblies 100, and more particularly with the articulating connectors 104.

The stabilizing rod 114 is configured to be secured to a plurality of vertebral anchor assemblies 100, which are configured to be secured to a plurality of vertebrae, such that the vertebrae can be fixated rigidly in relation to the stabilizing rod 114. A plurality of stabilizing rods 114 can be secured to different sets of the vertebral anchor assemblies 100, as may be required by surgical procedures for particular patients. For example, bilateral stabilizing rods 114 can be used to fixate vertebrae on opposing sides of the vertebrae. In some embodiments, a coupler (not shown) can be used to secure the bilateral stabilizing rods 114 to one another.

Figure 27:
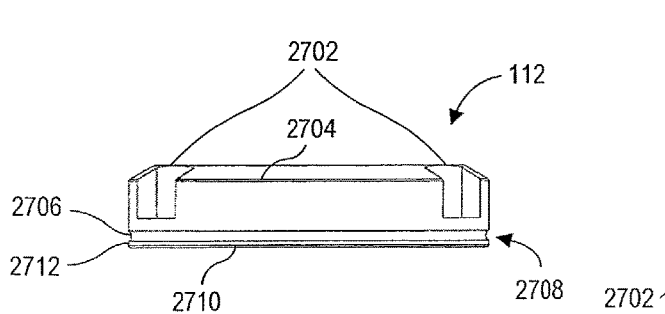
FIGS. 27 and 28 illustrate various views of a nut of FIG. 1.

FIG. 27 illustrates a side view of the nut 112 of FIG. 1. The nut 112 is configured to rotatably engage the thread 1704 of the saddle 108 and to be disposed in the seat 2304 of the washer 110. The nut 112 includes driver engagement recesses 2702, engagement lip 2708, and bottom 2710. Chamfers 2704 and 2712 can be provided.

The driver engagement recesses 2702 are configured to engage respective prongs of a driver tool (not shown) that can rotatably engage the nut 112 onto the thread 1704 of saddle 108. In some embodiments, there can be three equidistantly spaced recesses 2702 about the periphery of the nut 112. In different embodiments, there can be more or fewer recesses and the recess can be spaced or disposed in various configurations about the nut 112, such that a driver tool can engage and rotate the nut 112.

The chamfer 2704 is optional and can be provided to reduce the hardware profile of the vertebral anchor assembly 100 as well as to eliminate any sharp corners from the vertebral anchor assembly 100. Chamfer 2712 is configured to slideably engage chamfer 2506 (FIG. 25), facilitating the deflection of the engagement projections 2502 such that the nut 112 can be disposed in the seat 2304 of the washer 110.

A channel 2706 around the external lower periphery of nut 112 is provided to form an engagement lip 2708. In some embodiments, the channel 2706 can be omitted, and the engagement lip 2708 can extend out from the external periphery of the nut 112. In embodiments, where the washer 110 is omitted from the articulating connector 104, the channel 2706 and the engagement lip 2708 can be omitted as well.

The engagement lip 2708 is configured to friction fit the engagement projections 2502 of the washer 110. More specifically, the nut 112 is configured to snap into the seat 2404 by temporarily deflecting the engagement projections 2502.

The nut 112 includes a bottom 2710 configured to mate with the seat 2304 of the washer 110. In some embodiments, the bottom 2710 is flat and is configured to mate in a planar configuration with the seat 2304 of the washer 110. In other embodiments, different configurations of the bottom 2710 and seat 2304 can be selected such that the bottom 2710 and seat 2304 can mate with respect to one another.

Figure 28:
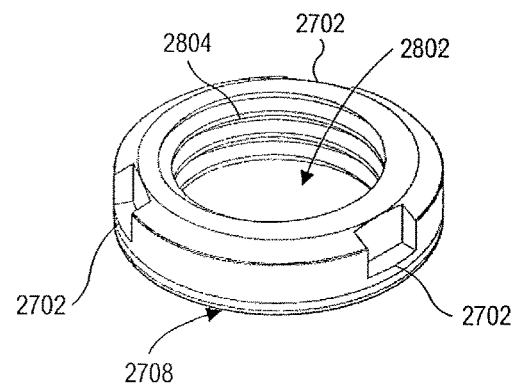

FIG. 28 illustrates a perspective view of the nut 112 of FIG. 1. The nut 112 also includes an opening 2802 and an internal thread 2804 along the opening 2802. The thread 2804 is configured to rotatably engage the thread 1708 of the saddle 108 when the nut 112 is rotated by a driver tool, which engages the respective recess 2702 of the nut 112.

The nut 112 can have a height from about 3.0 mm to about 4.0 mm. The opening (including thread 2804) 2802 in the nut 112 can have a diameter from about 11.0 mm to about 13.0 mm. The nut 112 can have an outside diameter from about 15.0 mm to about 16.0 mm. Alternate dimensions are possible based on the dimensions of the other components in the articulating connector 104, which can be based on different levels of the spine (e.g., cervical, lumbar, thoracic) and the patient.

FIG. 29 illustrates a front view of the polyaxial vertebral anchor assembly 100 with vertical adjustment and split lock of FIG. 1.

The vertebral anchor assembly 100 is configured to provide substantial configurability, including polyaxial articulation of the articulating connector 104 with respect to a vertebral anchor 102, rotational and height articulation of the articulating connector 104 with respect to a stabilizing rod 114, and common trajectory split lock via the post 106 of the articulating connector 104 to restrict the foregoing articulation of the vertebral anchor assembly 100 with respect to the vertebral anchor 102 and the stabilizing rod 114.

As illustrated, the vertebral anchor 102 is engaged (via thread 206) into a vertebra in a selected trajectory. The articulating connector 104 engages rigidly the vertebral anchor 102 in a selected polyaxial and rotational configuration with respect to the axis of the base member 502. More specifically, the connecting head end 210 of the vertebral anchor 102 engages rigidly at least a portion of the opening 1004 in the post 106 when engaged (pressed) via the setscrew 1200. The post 106 and the setscrew 1200 can be considered to provide the first lock of the common trajectory split lock. Specifically, the first lock engages rigidly the articulating connector 104 in the selected pivotal configuration with respect to the polyaxial vertebral anchor 102 through a common trajectory along an axis of the articulating connector 104 (e.g., axis of the cylinder 512).

As further illustrated, the stabilizing rod 114 is pressed into the saddle 108 (seat 1708) by the nut 112 (via pressure on the washer 110), which in turn forces engagement of the stabilizing rod 114 to the post 106 (via planar rails 604, 606) through the saddle 108 (via opening 1802) to engage rigidly the articulating connector 104 with respect to the stabilizing rod 114 in a selected height configuration. It is noted that in some embodiments, the washer 110 can be omitted. Accordingly, the post 106, saddle 108 and nut 112 can be considered to provide the second lock of the common trajectory split lock. It is noted that in some embodiments that include the washer 110, the lip 2708 of the nut 112 can engage in a friction-fit manner the engagement projections 2502 of the washer 110. Specifically, the second lock engages rigidly the stabilizing rod 114 at selected height and rotational configuration with respect to the polyaxial vertebral anchor 102 through the common trajectory along the axis of the articulating connector 104 (e.g., axis of the cylinder 512).

The first lock and second lock of the common trajectory split lock in the vertebral anchor assembly 100 can be engaged independently along a common trajectory in single wound (incision) of the patient. This provides or enables various surgical approaches (e.g., a minimally invasive surgical approach) to spinal fusion and/or deformity corrective surgery.

The polyaxial, rotational, and height articulation of the articulating connector 104 with respect to the vertebral anchor 102 and the stabilizing rod 114 can be adjusted through the common trajectory of the split lock. More specifically, the setscrew 1200 (FIG. 12) and the nut 112 (FIG. 1) can independently engage rigidly or loosen the particular components of the articulating connector 104 with respect to the vertebral anchor 102 and the stabilizing rod 114, respectively, through the common trajectory provided by the articulating connector 104, and more particularly by the post 106 of the articulating connector 104.

The respective locks of the split lock can be adjusted independently through the common trajectory of the post 106, e.g., setscrew 1200 can be engaged/loosened independently from the engagement/loosening of the nut 112. Accordingly, the vertebral anchor assembly 100 can be implanted, articulated and engaged rigidly along a common trajectory in single wound (incision) of the patient.

FIG. 30 illustrates a rear view of the polyaxial vertebral anchor assembly 100 with vertical adjustment and split lock of FIG. 1.

As illustrated, the opening 704 of the post 106 enables easier insertion of the connecting head end 210 of vertebral anchor 102 into the post 106. The arch 516 provides a greater polyaxial articulation (pivotal) to the articulating connector 104 about the polyaxial vertebral anchor 102.

FIG. 31 illustrates a top view of the polyaxial vertebral anchor assembly 100 with vertical adjustment and split lock of FIG. 1. As illustrated, the components of the articulating connector 104 can engage the stabilizing rod 114 in a selected height configuration.

Tightening (rotating) the nut 112 with respect to the saddle 108 presses the washer 110 into the stabilizing rod 114, which in turn causes the stabilizing rod 114 to rigidly engage the post 106, eliminating the slideable engagement of the articulating connector 104 with respect to the post 106 and setting the height with respect to the stabilizing rod 114.

Loosening the nut 112 with respect to the saddle 108 releases the pressure on the washer 110 and the stabilizing rod 114, which in turn releases its rigid engagement of the post 106 to allow height adjustment of the articulating connector 104 with respect to the stabilizing rod 114. After adjustment is completed, the nut 112 can be tightened, eliminating the slideable engagement of the articulating connector 104 with respect to the post 106 and setting the height with respect to the stabilizing rod 114.

FIG. 32 illustrates a bottom view of the polyaxial vertebral anchor assembly 100 with vertical adjustment and split lock of FIG. 1.

Tightening (rotating) the setscrew 1200 with respect to the post 106 causes the vertebral anchor 102 to rigidly engage the post 106, eliminating pivoting and rotational adjustment of the articulating connector 104 with respect to the vertebral anchor 102.

Loosening the setscrew 1200 with respect to the post 106 releases the vertebral anchor 102 from its rigid engagement with respect to the post 106 to allow pivoting and rotational adjustment of the articulating connector 104 with respect to the vertebral anchor 102. After adjustment is completed, the setscrew 1200 can be tightened, eliminating pivoting and rotational adjustment of the articulating connector 104 with respect to the vertebral anchor 102.

Figure 33:
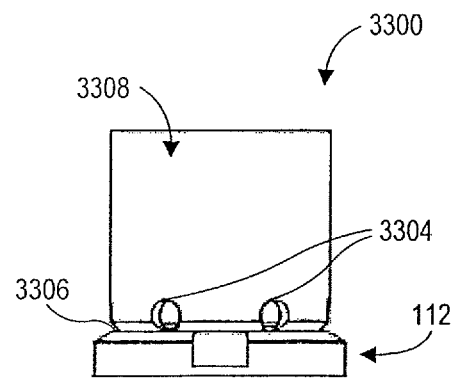
FIG. 33 illustrates a side view of an alternate nut.

FIG. 33 illustrates a side view of an alternate nut 3300. The nut 3300 can be utilized with the vertebral anchor assembly 100 instead of the nut 112. The nut 3300 includes the nut 112 that is connected to a breakaway extension 3302.

As described previously with respect to nut 112, the nut 3300 is likewise configured to rotatably engage the thread 1704 of the saddle 108 and can be disposed in the seat 2304 of the washer 110 (provided in certain embodiments). The breakaway extension 3302 can include at least one tool engagement recess 3308 (e.g., hex engagement recess) on the inside of the extension 3302 to engage one or more reciprocal extensions of a driver tool (not shown) configured to rotate the nut 3300 via the at least one tool engagement recess 3308.

The breakaway extension 3302 is connected to the nut 112 at 3306 and is configured to break away from the nut 112 when a predetermined amount of torque (pounds/inch) is reached, such that a price amount of pressure can be delivered to the stabilizing rod 114 via the nut 112 in order to engage rigidly the post 106 of the articulating connector 104.

A plurality of through openings 3304 are disposed about the lower periphery of the breakaway extension 3302 and are configured to weaken the connection between the nut 112 and the breakaway extension 3302 such that the breakaway extension 3302 can break off when the predetermined torque is reached as the nut 112 is tightened to engage rigidly the articulating connector 104.

Figure 34:
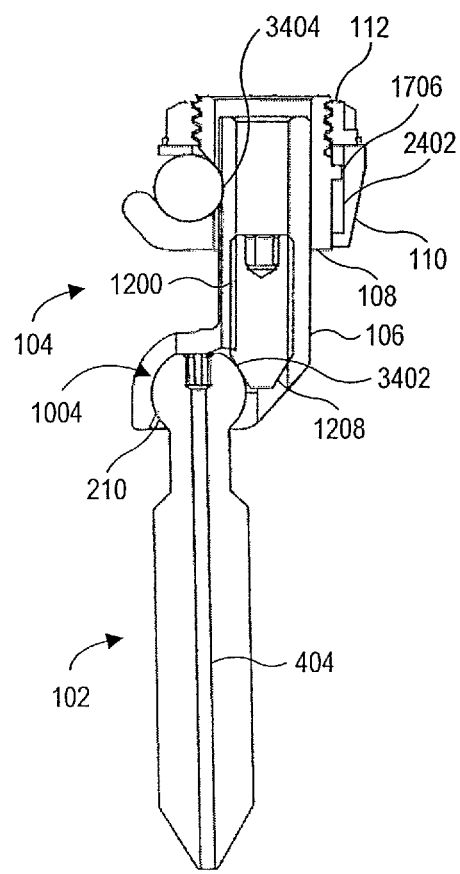
FIG. 34 illustrates a cross-sectional side view of the polyaxial vertebral anchor assembly with vertical adjustment and split lock of FIG. 1.

FIG. 34 illustrates a cross-sectional side view of the polyaxial vertebral anchor assembly 100 with vertical adjustment and split lock of FIG. 1.

The vertebral anchor assembly 100 provides substantial configurability. As illustrated, polyaxial articulation of the articulating connector 104 is provided with respect to a vertebral anchor 102. Further, rotational and height articulation of the articulating connector 104 is provided with respect to a stabilizing rod 114.

The split lock facilitates rigid engagement of the components in the vertebral anchor assembly 100 to eliminate the foregoing articulation with respect to the vertebral anchor 102 and the stabilizing rod 114 along a common trajectory.

As illustrated, the vertebral anchor 102 is engaged (via thread 206 not shown in FIG. 34) into a vertebra in a selected trajectory.

Rotation of the setscrew 1200 with respect to the post 106 through the common trajectory along the axis of the cylinder 512 engages the end 1208 of the setscrew 1200 to the connecting head end 210 of vertebral anchor 102 at an engagement point 3402. This engagement causes the connecting head end 210 of vertebral anchor 102 to engage rigidly a portion of the opening 1004 in the post 106 in a selected articulated (pivotal and rotational) configuration with respect to the axis of the base member 502.

Similarly, rotation of the nut 112 with respect to the saddle 108 through the common trajectory along the axis causes washer 110 to press the stabilizing rod 114 into the saddle 108. In some embodiments omitting the washer 110, the nut 112 can press the stabilizing rod 114 into the saddle 108. In turn, the stabilizing rod 114 engages rigidly the post 106 (via planar rails 604, 606 not shown in FIG. 34) through the saddle 108 in a selected articulated (height) configuration at an engagement point 3404.

The polyaxial, rotational, and height articulation of the articulating connector 104 with respect to the vertebral anchor 102 and the stabilizing rod 114, respectively, can be adjusted through the common trajectory split lock. More specifically, the setscrew 1200 and the nut 112 can engage rigidly or loosen the articulating connector 104 with respect to the vertebral anchor 102 and with respect to the stabilizing rod 114, respectively, through the common trajectory provided by the articulating connector 104, and more particularly by the post 106 of the articulating connector 104.

Moreover, the locks of the split lock can be adjusted independently through the common trajectory, e.g., setscrew 1200 can be engaged/loosened independently from the engagement/loosening of the nut 112. Accordingly, the vertebral anchor assembly 100 can be implanted, adjusted and locked with respect to the stabilizing rod 114 using various surgical approaches for spinal fusion and/or deformity correction, as described in the surgical or operative examples below.

In operation, the vertebral anchor assembly 100 can be implanted, adjusted and locked with respect to the stabilizing rod 114 via various surgical approaches, including the following example surgical approaches: open modular configuration; open assembled configuration; open long construct or deformity configuration; and minimally invasive configuration.

In accordance with the open modular configuration or surgical approach, the spine is situated at the bottom of a surgical trench and the muscles are retracted to the side of the trench. In this surgical approach, the vertebral anchor 102 is first secured to a vertebra in the trench.

The post 106 can then be secured (e.g., rigidly or semi-rigidly) to the vertebral anchor 102 via the setscrew 102, which can be preloaded into the post 106, e.g., the thread 1206 of the setscrew 1200 engaging the thread 1108 of the cylinder 512 in the post 106. The vertebra of the spine can be manipulated or adjusted (e.g., rotation, translation and/or other adjustments) using a rigid combination of the post 106 and vertebral anchor 102. The semi-rigid engagement can provide for articulation of the post with respect to the vertebral anchor 102 and with respect to the stabilizing rod 114.

Thereafter, a group or combination (sub-assembly) of the saddle 108, washer 110 and nut 112 (e.g., secured to one another semi-rigidly) can be slideably engaged onto the post 106. In some embodiments, the washer 110 can be omitted. It is noted that an extension tube, described with reference to FIG. 8, can be used to facilitate the slideable engagement of this combination onto the post 106.

The articulating rod 114 can be snapped into the saddle 108 and the nut 112 can be tightened. The extension tubes can then be removed. The common trajectory split lock of the vertebral anchor assembly 110 can be independently adjusted with respect to the vertebral anchor 102 and the stabilizing rod 114.

In accordance with the open assembled configuration or surgical approach, the vertebral anchor 102 is preassembled with the post 106 via the setscrew 1200. The combination of the vertebral anchor 102, post 106 and setscrew 1200 is implanted via the trench, securing the vertebral anchor 102 to a vertebra via the hole 804 of the post 106.

Similarly, the vertebra of the spine can be manipulated or adjusted (e.g., rotation, translation and/or other adjustments) using a rigid combination of the post 106 and the vertebral anchor 102. Further, the semi-rigid engagement can provide for articulation of the post with respect to the vertebral anchor 102 and with respect to the stabilizing rod 114.

Thereafter, a group or combination (sub-assembly) of the saddle 108, washer 110 and nut 112 (e.g., secured to one another semi-rigidly) can be slideably engaged onto the post 106. In some embodiments, the washer 110 can be omitted. Similarly, an extension tube can be used to facilitate the slideable engagement of this combination onto the post 106.

The articulating rod 114 can be snapped into the saddle 108 and the nut 112 can be tightened. The common trajectory split lock of the vertebral anchor assembly 110 can be independently adjusted (then secured rigidly) with respect to the vertebral anchor 102 and the stabilizing rod 114. The extension tubes can then be removed.

In accordance with the open long construct or deformity configuration or surgical approach, a plurality of vertebral anchors 102 is preassembled with a respective plurality of posts 106 via setscrews 1200. Extension tubes can be engaged to the cylinders 512 of the respective posts 106.

The plurality of combinations of the vertebral anchor 102, post 106 and setscrew 1200 is implanted via a trench, securing the vertebral anchors 102 to the vertebrae via the holes 804 of the respective posts 106. The vertebral anchors 102 can be engaged one or more at a time.

A plurality of groups or combinations (sub-assemblies) of the saddle 108, washer 110 and nut 112 for the respective vertebral anchors 102 can be engaged in a particular configuration to the stabilizing rod 114. In some embodiments, the washer 110 can be omitted.

The respective sub-assemblies secured to the stabilizing rod 114 can then be slideably engaged onto the respective posts 106 via the extension tubes. The common trajectory split locks of the vertebral anchor assemblies 100 can be independently adjusted and then tightened with respect to the respective vertebral anchors 102 and the stabilizing rod 114. The extension tubes can then be removed.

In accordance with the minimally invasive configuration or surgical approach, the spine is situated at the bottom of a narrowly retracted surgical channel via a surgical retractor. The vertebral anchor 102 is preassembled with the post 106 via the setscrew 1200 and the extension tube into a group or combination. The combination is then implanted through the surgical channel, securing the vertebral anchor 102 to a vertebra via hole 804 of the post 106.

Thereafter, a group or combination (sub-assembly) of the saddle 108, washer 110 and nut 112 (e.g., secured to one another semi-rigidly) can be slideably engaged onto the post 106 via the extension tube. In some embodiments, the washer 110 can be omitted. The stabilizing rod 114 is introduced or seated into the seat 1708 of the saddle 108 via a sub-fascial passage, for example, and the nut 112 can be tightened. Other applications or insertions of the stabilizing rod 114 are possible.

The common trajectory split lock of the vertebral anchor assembly 100 can be independently adjusted and then tightened with respect to the vertebral anchor 102 and the stabilizing rod 114 through the refracted channel along a common trajectory. The extension tubes can then be removed.

Thus, a polyaxial vertebral anchor assembly with vertical adjustment and split lock, vertebral anchor system and method have been described. Although specific example embodiments have been described, it will be evident that various modifications and changes may be made to these embodiments without departing from the broader scope of the invention.

Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments shown are described in sufficient detail to enable those skilled in the art to practice the teachings disclosed herein. Other embodiments may be utilized and derived therefrom, such that structural and logical substitutions and changes may be made without departing from the scope of this application.

The foregoing detailed description, therefore, is not to be taken in a limiting sense, and the scope of various embodiments is defined only by the appended claims, along with the full range of equivalents to which such claims are entitled.

Although specific embodiments have been shown and described herein, it should be appreciated that any arrangement calculated to achieve the same purpose may be substituted for the specific embodiments shown. This application is intended to cover any and all adaptations or variations of various embodiments. Combinations of the above embodiments and other embodiments not specifically described herein will be apparent to those of skill in the art upon reviewing the above description.

The Abstract is provided to comply with 37 C.F.R. § 1.72(b) and will allow the reader to quickly ascertain the nature of the technical disclosure of this application. It is submitted with the understanding that it will not be used to interpret or limit the scope or meaning of the claims.

In the foregoing detailed description, various features may be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

Moreover, it is contemplated that the features or components of various embodiments described herein can be combined into different combinations that are not explicitly enumerated in the foregoing detailed description and that such combinations can similarly stand on their own as separate example embodiments that can be claimed.

The invention claimed is:

1. A polyaxial vertebral assembly, the assembly comprising:
   a polyaxial vertebral anchor configured to penetrate and secure to a vertebra, the polyaxial vertebral anchor including a spherical head end; and
   an articulating connector including a base member, a cylindrical extension member, and a common trajectory split lock, the base member having a first axis and the cylindrical extension member having a second axis offset from the first axis, the common trajectory split lock comprising:
a first lock configured to engage rigidly the base member of the articulating connector in a selected pivotal configuration to the spherical head end of the polyaxial vertebral anchor along the second axis of the cylindrical extension member, the spherical head end of the polyaxial vertebral anchor disposed in the base member in the selected pivotal configuration with respect to the first axis of the base member; and
a second lock configured to engage rigidly a stabilizing rod at selected configurable height and rotational configuration with respect to the polyaxial vertebral anchor along the second axis of the cylindrical extension member, wherein the pivotal configuration and the height and rotational configuration are independently adjustable along the second axis of the common trajectory split lock.

2. The polyaxial vertebral assembly of claim 1, wherein the second lock of the articulating connector comprises:
a post including the base member and the cylindrical extension member extending from the base member, the post configured to engage a stabilizing rod at the selected height and rotational configuration with respect to the polyaxial vertebral anchor;
a saddle including a cylindrical body having an external thread and a seat extending in a curvilinear direction from the cylindrical body and having an opening into the cylindrical body, the saddle configured to slideably engage the post such that the post projects into the seat, the seat configured to engage a stabilizing rod; and
a nut having an internal thread configured to engage the external thread of the saddle until pressure on the stabilizing rod disposes the stabilizing rod into the seat of the saddle and the stabilizing rod rigidly engages the post that projects into the seat, fixating the selected height and rotational configuration with respect to the polyaxial vertebral anchor.

3. The polyaxial vertebral assembly of claim 2, wherein the articulating connector comprises:
a washer configured to be disposed between the saddle and the nut, the washer including a ring and a back extending below the ring, the ring configured to slideably engage the cylindrical body of the saddle such that the nut presses the stabilizing rod into the seat of the saddle via the washer.

4. The polyaxial vertebral assembly of claim 3, wherein the washer includes a seat and engagement projections extending from the seat that are configured to deflect with respect to nut such that the nut is disposed in the seat and the engagement projections engage a reciprocal lip of the nut.

5. The polyaxial vertebral assembly of claim 2, wherein the post comprises:
a pair of guide rails along the cylindrical extension that is configured to project into the seat of the saddle and to engage the stabilizing rod when the stabilizing rod is pressed into the seat of the saddle by the nut.

6. The polyaxial vertebral assembly of claim 2, wherein the cylindrical extension member of the post comprises:
an opening defined at least by an arch that is configured to provide pivotable insertion of the spherical head end of the polyaxial vertebral anchor into the base member of the post.

7. The polyaxial vertebral assembly of claim 6, wherein the base member of the post further comprises;

a first recess larger than the spherical head end of the polyaxial vertebral anchor and configured to receive the spherical head end in one or more trajectories with respect to the post through the opening;
a second recess smaller than the first recess and approximating the spherical head end of the polyaxial vertebral anchor, the second recess configured to facilitate articulation of the post with respect to the spherical head end and to secure the spherical head end in the second recess when the spherical head end of the polyaxial vertebral anchor is engaged by a setscrew; and
a ramp configured to facilitate transition between the first recess and second recess and insertion of the spherical head end of vertebral anchor into the second recess.

8. The polyaxial vertebral assembly of claim 7, wherein first recess and the second recess are approximately of a spherical shape.

9. The polyaxial vertebral assembly of claim 7, wherein the second recess includes a lip around at least a portion of the second recess configured to enable articulation of the spherical head end of the vertebral anchor in the second recess.

10. The polyaxial vertebral assembly of claim 1, wherein the first lock of the articulating connector comprises:
a post including the base member and the cylindrical extension member extending from the base member and having an internal thread, the base member of the post configured to engage the spherical head end of the polyaxial vertebral anchor in the selected pivotal configuration; and
a setscrew having an external thread configured to engage the internal thread of the extension member until pressure by the setscrew on the spherical head end of the polyaxial vertebral anchor engages rigidly the spherical head end of the polyaxial vertebral anchor into a portion of the base member in the selected pivotal configuration.

11. An articulating connector to secure a polyaxial vertebral anchor to a stabilizing rod, the articulating connector comprising:
a base member having a first axis and a cylindrical extension member having a second axis offset from the first axis; and
a common trajectory split lock comprising:
a first lock configured to engage rigidly the articulating connector in a selected pivotal configuration to a spherical head end of the polyaxial vertebral anchor along the second axis of the cylindrical extension member, the spherical head end of the polyaxial vertebral anchor disposed in the base member in the selected pivotal configuration with respect to the first axis of the base member; and
a second lock configured to engage rigidly a stabilizing rod at selected configurable height and rotational configuration with respect to the polyaxial vertebral anchor along the second axis of the cylindrical extension member, wherein the pivotal configuration and the height and rotational configuration are independently adjustable along the second axis of the common trajectory split lock.

12. The articulating connector of claim 11, wherein the second lock comprises:
a post including the base member and the cylindrical extension member extending from the base member, the post configured to engage a stabilizing rod at the selected height and rotational configuration with respect to the polyaxial vertebral anchor;

a saddle including a cylindrical body having an external thread and a seat extending in a curvilinear direction from the cylindrical body and having an opening into the cylindrical body, the saddle configured to slideably engage the post such that the post projects into the seat, the seat configured to engage a stabilizing rod; and a nut having an internal thread configured to engage the external thread of the saddle until pressure on the stabilizing rod disposes the stabilizing rod into the seat of the saddle and the stabilizing rod rigidly engages the post that projects into the seat, fixating the selected height and rotational configuration with respect to the polyaxial vertebral anchor.

13. The articulating connector of claim 12, further comprising:

a washer configured to be disposed between the saddle and the nut, the washer including a ring and a back extending below the ring, the ring configured to slideably engage the cylindrical body of the saddle such that the nut presses the stabilizing rod into the seat of the saddle via the washer.

14. The articulating connector of claim 13, wherein the washer includes a seat and engagement projections extending from the seat that are configured to deflect with respect to nut such that the nut is disposed in the seat and the engagement projections engage a reciprocal lip of the nut.

15. The articulating connector of claim 12, wherein the post comprises:

a pair of guide rails along the cylindrical extension that is configured to project into the seat of the saddle and to engage the stabilizing rod when the stabilizing rod is pressed into the seat of the saddle by the nut.

16. The articulating connector of claim 12, wherein the cylindrical extension member of the post comprises:

an opening defined at least by an arch that is configured to provide pivotable insertion of the spherical head end of the polyaxial vertebral anchor into the base member of the post.

17. The articulating connector of claim 16, wherein the base member of the post further comprises:

a first recess larger than the spherical head end of the polyaxial vertebral anchor and configured to receive the spherical head end in one or more trajectories with respect to the post through the opening;

a second recess smaller than the first recess and approximating the spherical head end of the polyaxial vertebral anchor, the second recess configured to facilitate articulation of the post with respect to the spherical head end and to secure the spherical head end in the second recess when the spherical head end of the polyaxial vertebral anchor engaged by a setscrew; and a ramp configured to facilitate transition between the first recess and second recess and insertion of the spherical head end of vertebral anchor into the second recess.

18. The articulating connector of claim 17, wherein first recess and the second recess are approximately of a spherical shape.

19. The articulating connector of claim 17, wherein the second recess includes a lip around at least a portion of the second recess configured to enable articulation of the spherical head end of the vertebral anchor in the second recess.

20. The articulating connector of claim 11, wherein the first lock of the articulating connector comprises:

a post including the base member and the cylindrical extension member extending from the base member and having an internal thread, the base member of the post configured to engage the polyaxial vertebral anchor in the selected pivotal configuration; and a setscrew having an external thread configured to engage the internal thread of the extension member until pressure by the setscrew on the spherical head end of the polyaxial vertebral anchor engages rigidly the spherical head end of the polyaxial vertebral anchor into a portion of the base member in the selected pivotal configuration.

21. A polyaxial vertebral system including at least one stabilizing rod, the system comprising:

a first polyaxial vertebral assembly comprising a first polyaxial vertebral anchor and a first articulating connector, the first polyaxial vertebral anchor configured to penetrate and secure to a first vertebra, the first polyaxial vertebral anchor including a first spherical head end, the first articulating connector including a first base member, a first cylindrical extension member, and a first common trajectory split lock, the first base member having a first axis and the first cylindrical extension member having a second axis offset from the first axis, the first common trajectory split lock comprising a first lock and a second lock, the first lock configured to engage rigidly the first base member of the first articulating connector in a first selected pivotal configuration to the first spherical head end of the first polyaxial vertebral anchor along the second axis of the first cylindrical extension member, the first spherical head end of the first polyaxial vertebral anchor disposed in the first base member in the first selected pivotal configuration with respect to the first axis of the first base member, the second lock configured to engage rigidly to the at least one stabilizing rod at first selected configurable height and rotational configuration with respect to the first polyaxial vertebral anchor along the second axis of the first cylindrical extension member; and a second polyaxial vertebral assembly comprising a second polyaxial vertebral anchor and a second articulating connector, the second polyaxial vertebral anchor configured to penetrate and secure to a second vertebra, the second polyaxial vertebral anchor including a second spherical head end, the second articulating connector including a second base member, a second cylindrical extension member, and a second common trajectory split lock, the second base member having a third axis and the second cylindrical extension member having a fourth axis offset from the third axis, the second common trajectory split lock comprising a third lock and a fourth lock, the third lock configured to engage rigidly the second base member of the second articulating connector in a second selected pivotal configuration to the second spherical head end of the second polyaxial vertebral anchor along the fourth axis of the second cylindrical extension member, the second spherical head end of the second polyaxial vertebral anchor disposed in the second base member in the second selected pivotal configuration with respect to the third axis of the second base member, the fourth lock configured to engage rigidly to the at least one stabilizing rod at second selected configurable height and rotational configuration with respect to the second polyaxial vertebral anchor along the fourth axis of the first cylindrical extension member; and wherein the first pivotal configuration and the second pivotal configuration, and the first height and rotational configuration and the second height and rotational configuration, are independently adjustable along the second axis of the first common trajectory split lock, and along the fourth axis of the second common trajectory split lock, respectively.

* * * * *